US012263247B2

(12) United States Patent
Denk

(10) Patent No.: US 12,263,247 B2
(45) Date of Patent: *Apr. 1, 2025

(54) INHALABLE COMPOSITIONS FOR USE IN THE TREATMENT OF PULMONARY DISEASES

(71) Applicant: Breath Therapeutics GmbH, Munich (DE)

(72) Inventor: Oliver Denk, Munich (DE)

(73) Assignee: Breath Therapeutics GmbH, Munich (DE)

(*) Notice: Subject to any disclaimer, the term of this patent is extended or adjusted under 35 U.S.C. 154(b) by 0 days.

This patent is subject to a terminal disclaimer.

(21) Appl. No.: 18/391,712

(22) Filed: Dec. 21, 2023

(65) Prior Publication Data

US 2024/0122852 A1 Apr. 18, 2024

Related U.S. Application Data

(63) Continuation of application No. 17/865,426, filed on Jul. 15, 2022, now Pat. No. 11,890,376, which is a (Continued)

(30) Foreign Application Priority Data

Dec. 4, 2018 (EP) .................................... 18210255

(51) Int. Cl.

*A61K 47/26* (2006.01)
*A61K 9/00* (2006.01)
(Continued)

(52) U.S. Cl.

CPC ............ *A61K 9/127* (2013.01); *A61K 9/0078* (2013.01); *A61K 38/13* (2013.01); *A61K 47/24* (2013.01);
(Continued)

(58) Field of Classification Search

None
See application file for complete search history.

(56) References Cited

U.S. PATENT DOCUMENTS 5,049,388 A * 9/1991 Knight .................. A61K 9/127 264/4.1
9,719,184 B2 * 8/2017 Xu ..................... B05B 17/0646
(Continued)

OTHER PUBLICATIONS

Weigt et al (Semin Respir Crit Care Med, Jun. 2013, 34(3), 336-351). (Year: 2013).*

*Primary Examiner* — Celeste A Roney
(74) *Attorney, Agent, or Firm* — Synergy IP Group AG; Lily Ackerman

(57) ABSTRACT

The present disclosure relates to a pharmaceutical composition comprising an inhalable immunosuppressive macrocyclic active ingredient for use in the prevention or treatment of a pulmonary disease or condition in a subject, wherein the pharmaceutical composition is administered to the subject by inhalation in form of an aerosol, and wherein the aerosol is generated by nebulization of the pharmaceutical composition using a nebulizer (100), the nebulizer comprising: a) an aerosol generator (101) comprising: —a fluid reservoir (103) for holding the pharmaceutical composition or an interface configured to connect a fluid reservoir, and a vibratable membrane (110) having a plurality of apertures, the apertures being adapted to produce an aerosol comprising droplets having a mass median aerodynamic diameter (MMAD) of up to about 4.0 gm as measured with a 0.9% (w/v) aqueous solution of sodium chloride; b) a chamber (105) for temporarily accommodating the aerosol generated by the aerosol generator (101), the chamber having an inner lumen with a volume in the range of from about 50 to about 150 ml; and c) a mouthpiece (40) for
(Continued)

delivering the aerosol supplied by the nebulizer (100) to the subject, the mouthpiece having an exhalation filter (30).

27 Claims, 3 Drawing Sheets

Related U.S. Application Data continuation of application No. 17/298,603, filed as application No. PCT/EP2019/083470 on Dec. 3, 2019, now Pat. No. 11,419,819.

(51) Int. Cl.

| | |
|---|---|
| ***A61K 9/127*** | (2006.01) |
| ***A61K 38/13*** | (2006.01) |
| ***A61K 47/24*** | (2006.01) |
| ***A61M 15/00*** | (2006.01) |

(52) U.S. Cl.

CPC ......... *A61K 47/26* (2013.01); *A61M 15/0085* (2013.01)

(56) References Cited

U.S. PATENT DOCUMENTS

| | | | | | |
|---|---|---|---|---|---|
| 2004/0040557 | A1* | 3/2004 | Salter | A61M 15/0021 | 128/203.12 |
| 2006/0110441 | A1* | 5/2006 | Wong | A61K 31/4706 | 514/217 |
| 2008/0299049 | A1* | 12/2008 | Stangl | A61M 15/0086 | 128/200.14 |
| 2013/0177626 | A1* | 7/2013 | Keller | A61K 9/0014 | 514/19.9 |

* cited by examiner

INHALABLE COMPOSITIONS FOR USE IN THE TREATMENT OF PULMONARY DISEASES

CROSS REFERENCE TO RELATED APPLICATIONS

This application is a continuation of U.S. application Ser. No. 17/865,426, filed on Jul. 15, 2022, now U.S. Pat. No. 11,890,376 B2, which is a continuation of U.S. application Ser. No. 17/298,603, filed on May 31, 2021, now U.S. Pat. No. 11,419,819 B2, which is a U.S. National Stage Application filed under 35 U.S.C. § 371 claiming the benefit of PCT Application No. PCT/EP2019/083470, filed on Dec. 3, 2019, which claims priority to and the benefit of European Application No. 18210255.8, filed on Dec. 4, 2018, all of which are incorporated herein by reference in their entireties.

TECHNICAL FIELD

The present invention relates to pharmaceutical compositions comprising an inhalable immunosuppressive macrocyclic active ingredient for use in the prevention or treatment of a pulmonary disease or condition in a subject. The pharmaceutical compositions of the present invention can be administered by inhalation of an aerosol generated with a nebulizer comprising a vibratable membrane as well as a mixing chamber.

BACKGROUND

WO 2007/065588 A1 discloses liquid pharmaceutical compositions comprising a therapeutically effective dose of a cyclosporin, an aqueous carrier liquid, a first solubilizing substance selected among the group of phospholipids, and a second solubilizing substance selected among the group of non-ionic surfactants, i.a. suitable for pulmonary application in the form of an aerosol.

Pharmaceutical compositions as described above may be inhaled by a subject in need thereof. It should be noted that the cyclosporines, such as cyclosporine A, just as many other macrocyclic immunosuppressive compounds are very potent medications for the suppression of an immune response in a patient in need of such a treatment. In other individuals which do not need or undergo an immunosuppressive treatment, however, these potent compounds can have unwanted if not dangerous effects upon exposure.

In cases in which an immunosuppressive or other potent medication is to be administered by inhalation, usually a nebulizer is necessary to provide for the corresponding aerosol comprising such medication, often in form of an aerosol. In use of such nebulizers, however, some nebulized liquid will be discharged from the nebulizer during exhalation by the user. In particular, known nebulizers of this type comprise an ambient opening and an exhalation opening each comprising a one-way valve allowing that ambient air is drawn into the nebulizer during inhalation and allowing air to escape the nebulizer during exhalation. A nebulizer of this type is, for example, disclosed in EP 1 927 373 B1.

In some instances, as mentioned above, the liquid to be nebulized/aerosolized may contain compounds which are detrimental for individuals staying in the environment in which the patient inhales even though they serve a therapeutic purpose with respect to the disease of the patient. It is known in the art to use exhalation filters so as to avoid those components from being discharged (exhausted) into the environment. One example showing such an exhalation filter is EP 1 868 570 B1.

Furthermore, especially in view of the above-described problem and in view of the fact that a macrocyclic immunosuppressant such as cyclosporine A should be administered in the minimal amount possible and exclusively or predominantly to the targeted tissues, there is still need for a pharmaceutical composition comprising an macrocyclic immunosuppressant for inhalation purposes that allows for an effective delivery of the chosen immunosuppressive wherein as much as possible of the administered immunosuppressive is actually delivered to the targeted tissues and a minimized amount of the compound to be administered is exhaled by the patient during administration. Furthermore, there is still a need for an improved transport of macrocyclic immunosuppressants especially to the peripheral tissues of the lungs.

It is therefore an object of the present invention to provide for a pharmaceutical composition comprising a macrocyclic immunosuppressant useful for the treatment or prevention of a pulmonary disease or condition in a subject in need thereof that can be administered by inhalation whereby

- the immunosuppressant is administered in a form that allows for the delivery of the maximum amount or fraction actually delivered to the target tissue; and
- the amount or fraction of the administered immunosuppressant that is not delivered to the target tissue and exhaled by the subject is minimized.

Further objects of the present invention will become apparent from the present disclosure including the examples and claims.

SUMMARY OF THE INVENTION

In a first aspect, the present invention provides a pharmaceutical composition comprising an inhalable immunosuppressive macrocyclic active ingredient for use in the prevention or treatment of a pulmonary disease or condition in a subject,

- wherein the pharmaceutical composition is administered to the subject by inhalation in form of an aerosol, and
- wherein the aerosol is generated by nebulization of the pharmaceutical composition using a nebulizer (100), the nebulizer comprising:
- a) an aerosol generator (101) comprising:
  - a fluid reservoir (103) for holding the pharmaceutical composition or an interface configured to connect a fluid reservoir, and
  - a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;
- b) a chamber (105) for temporarily accommodating the aerosol generated by the aerosol generator (101), the chamber having an inner lumen with a volume in the range of from about 50 to about 150 ml; and
- c) a mouthpiece (40) for delivering the aerosol supplied by the nebulizer (100) to the subject, the mouthpiece having an exhalation filter (30).

In a second aspect, the present invention provides for a method for preventing or treating a pulmonary disease or condition in a subject, the method comprising the step of administering an inhalable immunosuppressive macrocyclic active ingredient to said subject by inhalation in form of an aerosol comprising the immunosuppressive macrocyclic active ingredient, preferably in liposomally solubilized form, wherein the aerosol is generated by nebulization of the pharmaceutical composition using a nebulizer (100), the nebulizer comprising:

a) an aerosol generator (101) comprising:

a fluid reservoir (103) or an interface configured to connect a fluid reservoir, and a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;

b) a chamber (105) for temporarily accommodating the aerosol generated by the aerosol generator, the chamber having an inner lumen with a volume in the range of from about 50 to about 150 ml; and c) a mouthpiece (40) for delivering the aerosol supplied by the nebulizer (100) to the subject, the mouthpiece having an exhalation filter (30).

In a third aspect, the present invention provides for a kit comprising a pharmaceutical composition comprising an inhalable immunosuppressive macrocyclic active ingredient for use in the prevention or treatment of a pulmonary disease or condition in a subject; and a nebulizer (100), the nebulizer comprising:

a) an aerosol generator (101) comprising:

a fluid reservoir (103) for holding the pharmaceutical composition or an interface configured to connect a fluid reservoir, and a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;

b) a chamber (105) for temporarily accommodating the aerosol generated by the aerosol generator (101), the chamber having an inner lumen with a volume in the range of from about 50 to about 150 ml; and c) a mouthpiece (40) for delivering the aerosol supplied by the nebulizer (100) to the subject, the mouthpiece having an exhalation filter (30).

DETAILED DESCRIPTION OF THE INVENTION

Figure 1:
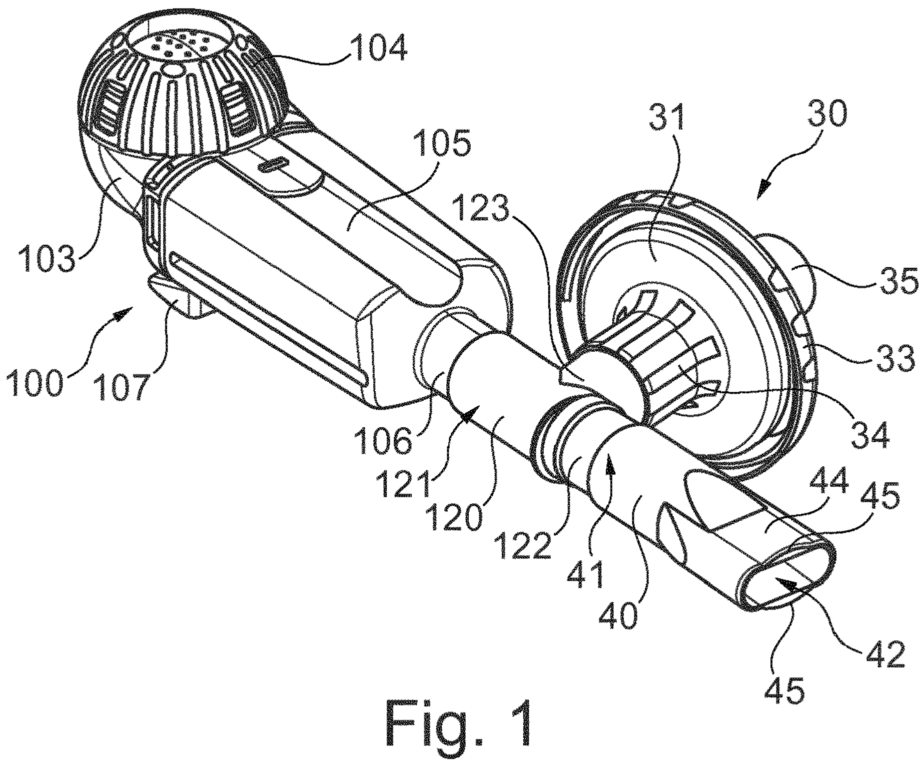
FIG. 1 shows a perspective view of a nebulizer useful for the administration of the inhalable immunosuppressive macrocyclic active ingredient according to the present invention with an exhalation filter attached to the nebulizer via a T-shaped adapter, wherein the filter is directed to the right in front view and a separate mouthpiece is connected to the adapter.

The terms "consist of", "consists of" and "consisting of" as used herein are so-called closed language meaning that only the mentioned components are present. The terms "comprise", "comprises" and "comprising" as used herein are so-called open language, meaning that one or more further components may or may not also be present.

The term "active ingredient" or "active pharmaceutical ingredient" (also referred to as "API" throughout this document) refers to any type of pharmaceutically active compound or derivative that is useful in the prevention, diagnosis, stabilization, treatment, or—generally speaking—management of a condition, disorder or disease.

The term "therapeutically effective amount" as used herein refers to a dose, concentration or strength which is useful for producing a desired pharmacological effect. In the context of the present invention, the term "therapeutically effective" also includes prophylactic activity. The therapeutic dose is to be defined depending on the individual case of application. Depending on the nature and severity of the disease, route of application as well as height and state of the patient, a therapeutic dose is to be determined in a way known to the skilled person.

In the context of the present invention, a "pharmaceutical composition" is a preparation of at least one API and at least one adjuvant, which, in the simplest case, can be, for example, an aqueous liquid carrier such as water or saline.

'A' or 'an' does not exclude a plurality; i.e. the singular forms 'a', 'an' and 'the' should be understood as to include plural referents unless the context clearly indicates or requires otherwise. In other words, all references to singular characteristics or limitations of the present disclosure shall include the corresponding plural characteristic or limitation, and vice versa, unless explicitly specified otherwise or clearly implied to the contrary by the context in which the reference is made. The terms 'a', 'an' and 'the' hence have the same meaning as 'at least one' or as 'one or more' unless defined otherwise. For example, reference to 'an ingredient' includes mixtures of ingredients, and the like.

When used herein, the term 'about' or 'ca.' will compensate for variability allowed for in the pharmaceutical industry and inherent in pharmaceutical products, such as differences in content due to manufacturing variation and/or time-induced product degradation. The term allows for any variation, which in the practice of pharmaceuticals would allow the product being evaluated to be considered bioequivalent in a mammal to the recited strength of a claimed product.

'Essentially', 'about', 'approximately', 'substantially" and the like in connection with an attribute or value include the exact attribute or the precise value, as well as any attribute or value typically considered to fall within a normal range or variability accepted in the technical field concerned. For example, 'substantially free of water" means that no water is deliberately included in a formulation, but does not exclude the presence of residual moisture.

In the context of the present invention, a "colloidal aqueous solution" preferably means a solution without organic solvent consisting of mainly unilamellar liposomes having a mean diameter of at most 100 nm and/or a polydispersity index (PI) of not more than 0.50 in which the active agent is, at least predominantly, dissolved. Preferably, water, or more specifically saline is the only liquid solvent contained in the preparation.

Furthermore, it is preferred that the preparation is an aqueous solution or an aqueous colloidal solution, i.e., a monophasic liquid system. Such a system is essentially free of dispersed particles having a greater than colloidal particle size. By convention, particles below about 1 μm are regarded as colloidal particles which do not constitute a separate phase and do not result in a physical phase boundary. Sometimes, particles in a size range just above 1 μm are also still considered colloidal. Preferably, however, colloidal aqueous solutions as used herein are essentially free of particles which do clearly not belong to the colloidal spectrum, i.e., for example, particles having a diameter of 1 μm or more.

In a first aspect, the present invention provides a pharmaceutical composition comprising an inhalable immunosuppressive macrocyclic active ingredient for use in the prevention or treatment of a pulmonary disease or condition in a subject, wherein the pharmaceutical composition is administered to the subject by inhalation in form of an aerosol, and wherein the aerosol is generated by nebulization of the pharmaceutical composition using a nebulizer (100), the nebulizer comprising:

a) an aerosol generator (101) comprising:
   a fluid reservoir (103) for holding the pharmaceutical composition or an interface configured to connect a fluid reservoir, and
   a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;
b) a chamber (105) for temporarily accommodating the aerosol generated by the aerosol generator (101), the chamber having an inner lumen with a volume in the range of from about 50 to about 150 ml; and
c) a mouthpiece (40) for delivering the aerosol supplied by the nebulizer (100) to the subject, the mouthpiece having an exhalation filter (30).

The pharmaceutical compositions for use according to the present invention comprising an inhalable immunosuppressive macrocyclic active ingredient are useful in the prevention or treatment of a broad variety of pulmonary diseases or conditions in a subject. The term 'subject' as used herein means a mammal, more specifically a human, being diagnosed with such pulmonary diseases or conditions or being threatened to develop such diseases or conditions. In specific embodiments, term 'subject' as used herein means a human or patient being diagnosed with a pulmonary disease or condition and in need of a treatment thereof.

In specific embodiments, the pulmonary disease or condition to be treated by administration of the compositions for use according to the present invention is selected from the group consisting of the pulmonary diseases asthma, refractory asthma, chronic obstructive bronchitis, parenchymal, fibrotic and interstitial lung diseases and inflammations, bronchiolitis obliterans (BOS), and acute and chronic organ transplant rejection reactions after lung transplantations and the diseases resulting therefrom. In further specific embodiments, the pulmonary disease or condition is bronchiolitis obliterans (BOS), optionally after acute and chronic organ transplant rejection reactions after lung transplantation or after hematopoietic stem cell transplantation (HSCT).

In further specific embodiments, the pharmaceutical composition for use according to the present invention are useful for the treatment of a pulmonary disease or condition or for the prevention or delay of progression of such pulmonary disease or condition as described above, for example BOS, in a subject or patient being diagnosed with such disease or condition, specifically with BOS. The existence of BOS, for example, can be determined on the basis of spirometric measurements of the forced expiratory volume (FEV). Preferably, the reduction of the forced expiratory volume in one second ($FEV_1$) is used as an indicator of the existence of BOS and, accordingly, for the risk of pulmonary chronic graft rejection. $FEV_1$ measurements can be performed according to current American Thoracic Society (ATS)/European Respiratory Society (ERS) spirometry guidelines. The forced expiratory volume in one second ($FEV_1$) is expressed in litre (L).

Bronchiolitis obliterans (BOS) can be graded according to the degree of progression of this pulmonary disease as described in Estenne M, et al. Bronchiolitis obliterans syndrome 2001: an update of the diagnostic criteria. *J Heart Lung Transplant* 2002; 21(3): 297-310. Based on the percentage of decrease of the forced expiratory volume in one second ($FEV_1$), BOS can be graded as follows:

BOS 0: $FEV_1$>90% of baseline
BOS 0-p: $FEV_1$ 81% to 90% of baseline
BOS 1: $FEV_1$ 66% to 80% of baseline
BOS 2: $FEV_1$ 51% to 65% of baseline
BOS 3: $FEV_1$ 50% or less of baseline The compositions for use according to the present invention may be particularly useful in the treatment or for the prevention or delay of the progression of BOS grade I (BOS 1) or higher, more specifically of BOS grade I or II or even more specifically BOS grade I (BOS 1).

The pharmaceutical compositions for use according to the present invention, in specific embodiments, may be liquid compositions. In these embodiments, the compositions for use according to the present invention comprise an inhalable immunosuppressive macrocyclic active ingredient and a liquid carrier or vehicle in which the active ingredient can be dissolved, dispersed or suspended. Accordingly, in specific embodiments, the pharmaceutical composition for use according to the present invention is a liquid composition comprising an aqueous liquid vehicle. In further specific embodiments, the liquid vehicle is an aqueous liquid vehicle which may comprise water and optionally one or more physiologically acceptable organic solvents, such as ethanol or propylene glycol or others, preferably, however, ethanol and/or propylene glycol. In further specific embodiments, the liquid vehicle comprises one or more pharmaceutically acceptable salts such as sodium chloride (NaCl). Accordingly, the liquid vehicle may comprise saline or may essentially consist of saline. In these specific embodiments as well as in other embodiments, in which the aqueous liquid vehicle comprises further constituents or solvents, the concentration of sodium chloride can range from about 0.1 to about 7% (w/v) or from about 0.1 to about 3% (w/v) or from about 0.1 to about 0.9% (w/v). Preferably, a saline solution with a sodium chloride concentration of about 0.25% (w/v) is used, wherein the term "w/v" means the weight of the dissolved sodium chloride per volume of the liquid vehicle comprised by the aqueous liquid composition.

The pharmaceutical compositions for use according to the present invention further comprise an inhalable macrocyclic immunosuppressive active ingredient. Examples of such inhalable macrocyclic immunosuppressive active ingredients comprise, but are not limited to cyclosporine A (CsA), tacrolimus, sirolimus and/or everolimus, preferably in a therapeutically effective amount. An immunosuppressive compound as named above may be present as the only active ingredient or in form of a mixture of two or more different inhalable immunosuppressive macrocyclic active ingredients, optionally in combination with other non-immunosuppressive and/or non-macrocyclic active ingredients. In specific embodiments, however, the pharmaceutical compositions for use according to the present invention comprise just one inhalable immunosuppressive macrocyclic active ingredient.

In preferred embodiments, however, the inhalable immunosuppressive macrocyclic active ingredient is selected from cyclosporine A (CsA) and tacrolimus. In further preferred embodiments, the inhalable immunosuppressive active ingredient comprised by the present pharmaceutical compositions for use is cyclosporine A (ciclosporin A; CsA (cyclo-[[(E)-(2S,3R,4R)-3-hydroxy-4-methyl-2-(methylamino)-6-octenoyl]-L-2-aminobutyryl-N-methylglycyl-N-methyl-L-leucyl-L-valyl-N-methyl-L-leucyl-L-alanyl-D-alanyl-N-methyl-L-leucyl-N- methyl-L-leucyl-N-methyl-L-valyl]). Pharmaceutical compositions comprising CsA or more specifically L-CsA are known e.g. from US 2009169607 A1 and can be prepared accordingly.

In other embodiments, however, the inhalable macrocyclic immunosuppressive active ingredient comprised by the present pharmaceutical compositions for use is tacrolimus.

It should be noted that the inhalable macrocyclic immunosuppressants as described above, especially cyclosporine A (CsA) and tacrolimus are very potent active compounds which show immunomodulating effects in a patient or other individual when exposed to very low amounts or concentrations of these compounds. As already noted above, however, this may be detrimental or even hazardous for individuals staying in the environment in which the patient inhales even though they serve a therapeutic purpose with respect to the disease of the patient. On this basis, it is especially important to provide for nebulizer or mouthpiece that allows for the effective administration of aerosols comprising such compounds to a patient while minimizing the risk for unwanted exposures of individuals other than the patient by exhalation of these compounds, or more specifically, the portion of these active ingredients which have not been absorbed by the patient during inhalation.

In specific embodiments, the pharmaceutical composition for use according to the present invention, more specifically the liquid pharmaceutical compositions for use according to the present invention comprise the selected immunosuppressive macrocyclic active ingredient, especially cyclosporine A (CsA) or tacrolimus, preferably cyclosporine A (CsA) in a concentration in the range of from about 1 mg/mL to about 10 mg/mL, preferably from about 2 mg/mL to about 8 mg/mL, more preferably from 2.5 mg/mL to about 6 mg/mL, even more preferably from 3 mg/mL to about 4 mg/mL, especially at a concentration of about 4 mg/mL.

In further specific embodiments, in the pharmaceutical compositions for use according to the present invention, the inhalable immunosuppressive active ingredient, especially cyclosporine A, is present in liposomally solubilized form (L-CsA). In such cases in which liquid, preferably aqueous liquid pharmaceutical compositions for use according to the present invention comprise cyclosporine A in liposomally solubilized form (L-CsA), the corresponding concentration of L-CsA may be in the range of from about 3 mg/mL to about 5 mg/mL, more specifically in the range of from about 3.8 mg/mL to about 4.2 mg/mL.

In further specific embodiments, especially in which the present pharmaceutical compositions for use comprise the inhalable immunosuppressive macrocyclic active ingredient in liposomally solubilized form, the pharmaceutical composition in liquid form may be obtained by reconstitution of a lyophilisate comprising the immunosuppressive macrocyclic active ingredient and liposome forming structures.

Such liposome forming structures may further comprise a membrane-forming substance selected from the group of phospholipids or two or more different membrane-forming substances selected from the group of phospholipids. The term "membrane-forming substance" as used herein means that the substance is capable of forming a lipid bilayer membrane by self-assembly in an aqueous carrier liquid, such as water or saline and/or is capable of forming liposomes in an aqueous carrier liquid under circumstances as described in further detail below.

The liposome-forming structures that may be comprised by the present pharmaceutical compositions may comprise a bilayer membrane formed of the membrane-forming substance selected from the group of phospholipids. The liposome-forming structures may or may not have a continuous or closed bilayer membrane. In specific embodiments, the liposome-forming structures are at least partly present in unilamellar form or, preferably, are predominantly present in unilamellar form. The term "unilamellar" as used herein means that the corresponding liposome-forming structures only comprise a single layer formed by a single lipid bilayer membrane and not a plurality of lipid bilayer membranes in a layered arrangement.

In specific embodiments, the inhalable macrocyclic immunosuppressive ingredient, specifically CsA that may be comprised by liposome-forming structures as described above is at least partially incorporated (or intercalated) in the bilayer membrane of the liposome-forming structures. The term "incorporated" as used herein means, with regard to CsA being a lipophilic compound, that CsA is located or intercalated in the inner lipophilic part of the bilayer lipid membrane rather than on the hydrophilic outer surfaces of the lipid bilayer membrane (whereas the terms surfaces can mean both surfaces, or more specifically the inner or outer surface of the bilayer membrane forming the liposome-forming structures). In further embodiments, the inhalable immunosuppressive macrocyclic active ingredient, specifically CsA or L-CsA is predominantly (for example by at least about 90% or even at least about 95% to about 97.5%) incorporated in the bilayer membrane of the liposome-forming structures.

Phospholipids that may be comprised by the liposome forming structures of the present invention are, in particular, mixtures of natural or enriched phospholipids, for example, lecithins such as the commercially available Phospholipon® G90, 100, or Lipoid 90, S 100.

Phospholipids are amphiphilic lipids which contain phosphorus. Known also as phosphatides, they play an important role in nature, especially as the double layer forming constituents of biological membranes and frequently used for pharmaceutical purposes are those phospholipids which are chemically derived from phosphatidic acid. The latter is a (usually doubly) acylated glycerol-3-phosphate in which the fatty acid residues may be of different lengths. The derivatives of phosphatidic acids are, for example, the phosphocholines or phosphatidylcholines, in which the phosphate group is additionally esterified with choline, as well as phosphatidylethanolamine, phosphatidylinositols etc. Lecithins are natural mixtures of various phospholipids which usually contain a high proportion of phosphatidylcholines. Preferred phospholipids according to the invention are lecithins as well as pure or enriched phosphatidylcholines such as dimyristoylphospatidylcholine, di-palmitoyl-phosphatidylcholine and distearoylphosphatidylcholine. Accordingly, in preferred embodiments, the membrane-forming substance selected from the group of phospholipids is a mixture of natural phospholipids.

In preferred embodiments, the membrane-forming substance selected from the group of phospholipids is a lecithin containing unsaturated fatty acid residues. In yet further preferred embodiments, the membrane-forming substance selected from the group of phospholipids is a lecithin selected from the group consisting of soy bean lecithin, Lipoid S100, Phospholipon® G90, 100 or a comparable lecithin. In further preferred embodiments, the membrane-forming substance selected from the group of phospholipids is selected from Lipoid S100, Lipoid S75, particularly Lipoid S100.

The pharmaceutical compositions for use according the present invention or, more specifically, the liposome-forming structures that may be comprised by the present pharmaceutical compositions may further comprise a solubility-enhancing substance or two or more different solubility-enhancing substances selected from the group of non-ionic surfactants. Non-ionic surfactants have—as other surfactants—at least one rather hydrophilic and at least one rather lipophilic molecular region. There are monomeric, low molecular weight non-ionic surfactants and non-ionic surfactants having an oligomeric or polymeric structure. Examples of suitable non-ionic surfactants suitable as solubility-enhancing substances of the liposome-forming structures as described above comprise polyoxyethylene alkyl ethers, polyoxyethylene sorbitan fatty acid esters such as, for example, polyoxyethylene sorbitan oleate, sorbitan fatty acid esters, poloxamers, vitamin E-TPGS (D-a-tocopheryl polyethylene glycol 1000 succinate) and tyloxapol.

In specific embodiments, the solubility-enhancing substance selected from the group of non-ionic surfactants is selected from the group of polysorbates and vitamin E-TPGS, preferably is selected from the group of polysorbates. In a particularly preferred embodiment, the solubility-enhancing substance selected from the group of non-ionic surfactants is polysorbate 80.

In specific embodiments of the present pharmaceutical compositions, the amount of the membrane-forming substance selected from the group of phospholipids, preferably the lecithin is larger than the amount of the solubility-enhancing substance selected from the group of non-ionic surfactants. In exemplary embodiments, the weight ratio of the membrane forming substance (or the sum of the membrane-forming substances) selected from the group of phospholipids, preferably the lecithin, to the solubility enhancing substance (or the sum of the solubility enhancing substances) selected from the group of non-ionic surfactants, preferably the polysorbate, is selected in the range of from about 15:1 to about 9:1, preferably from about 14:1 to about 12:1, for example, about 13:1.

In further specific embodiments, the weight ratio between the (sum of the) membrane-forming substance(s) selected from the group of phospholipids and the solubility-enhancing substance selected from the group of non-ionic surfactant on the one hand and the immunosuppressive macrocyclic active ingredient, preferably CsA, on the other hand is selected in the range of from about 5:1 to about 20:1, preferably from about 8:1 to about 12:1 and more preferably about 10:1.

In yet further specific embodiments, the weight ratio between the membrane-forming substance selected from the group of phospholipids, preferably the lecithin, the solubility-enhancing substance selected from the group of non-ionic surfactants, preferably the polysorbate and the immunosuppressive macrocyclic active ingredient, preferably CsA, is selected in the range of from about 15:1:1.5 to about 5:0.3:0.5, and preferably at about 9:0.7:1.

The pharmaceutical composition for use according to the present invention may further comprise one or more further excipients. Suitable excipients are known to the skilled person. For example, the present pharmaceutical compositions can optionally contain pH-correcting agents in order to adjust the pH, such as physiologically acceptable bases, acids or salts, optionally as buffer mixtures. In this context, the term "physiologically acceptable" does not mean that one of the excipients must be tolerable an its own and in undiluted form, which would not be the case, for example, for sodium hydroxide solution, but means that it must be tolerable at the concentration in which it is contained in the lyophilized pharmaceutical composition, especially after reconstitution.

Suitable pH-correcting agents or buffers for adjusting the pH may be selected, inter alia, with regard to the intended route of application. Examples for potentially useful excipients of this group comprise sodium hydroxide solution, basic salts of sodium, calcium or magnesium such as, for example, citrates, phosphates, acetates, tartrates, lactates etc., amino acids, acidic salts such as hydrogen phosphates or dihydrogen phosphates, especially those of sodium, moreover, organic and inorganic acids such as, for example, hydrochloric acid, sulphuric acid, phosphoric acid, citric acid, cromoglycinic acid, acetic acid, lactic acid, tartaric acid, succinic acid, fumaric acid, lysine, methionine, acidic hydrogen phosphates of sodium or potassium etc.

In some embodiments, a liquid aqueous pharmaceutical composition for use according to the present invention comprises buffers to ensure a neutral or acidic pH of the pharmaceutical composition after reconstitution. Preferably, the pH of the present pharmaceutical composition is in the range of at most about 8.5 or in the range of about 2.5 to about 7.5. For pulmonary or parenteral application, a pH of about 4 to about 7.5 is preferred, provided that this is compatible with other requirements of the formulation such as, for example, stability aspects. Particularly preferred is a pharmaceutical composition which is buffered with a phosphate buffer to ensure a pH in the range of 6.0 to 7.5 or from 6.0 to 7.0 or in the range of from 6.3 to 6.7, whereby the stability of the composition can be markedly improved and the occurrence of undesirable lysolecithin during storage can be effectively reduced.

Furthermore, the present pharmaceutical composition, especially when in form of an aqueous liquid, may or may not contain osmotically active adjuvants in order to adjust it to a desired osmolality, which is important in certain applications such as especially for inhalation, in order to achieve good tolerability. Such adjuvants are frequently referred to as isotonizing agents even if their addition does not necessarily result in an isotonic composition after reconstitution, but in an isotonicity close to physiological osmolality in order to achieve the best possible physiological tolerability.

A particularly frequently used isotonizing agent is sodium chloride. In another embodiment, the present pharmaceutical compositions contain an essentially neutral salt as isotonizing agent which is not sodium chloride, but, for example, a sodium sulphate or sodium phosphate. It should be noted, however, that the isotonizing agent may also be comprised by the aqueous vehicle or carrier liquid as described above, for example in form of an aqueous solution of sodium chloride (saline). In this case, however, salts other than sodium salts may be also preferable. Thus, it is known that certain calcium and magnesium salts have a positive or supporting effect in the inhalation of active agent solutions, possibly because they themselves counteract the local irritations caused by the administration and because they have a bronchodilatory effect which is currently postulated in the clinical literature (for example Hughes et al., Lancet. 2003;

361 (9375): 2114-7) and/or because they inhibit the adhesion of germs to the proteoglycans of the mucosa of the respiratory tract so that the mucociliary clearance as the organism's natural defense against pathogens is supported indirectly (K. W. Tsang et al., Eur. Resp. 2003. 21, 932-938). Advantageous may be, for example, magnesium sulphate, which has excellent pulmonary tolerability and can be inhaled without concern, as well as calcium chloride (1-10 mmol).

In further specific embodiments, the pharmaceutical compositions for use according to the present invention comprise one or more further excipients which are selected from buffers and chelating agents. Exemplary compounds suitable as buffers for the adjustment of the pH of the present pharmaceutical compositions after reconstitution comprise, for example, sodium dihydrogen phosphate dihydrate and/or disodium hydrogen phosphate dodecahydrate, sodium hydroxide solution, basic salts of sodium, calcium or magnesium such as, for example, citrates, phosphates, acetates, tartrates, lactates etc., amino acids, acidic salts such as hydrogen phosphates or dihydrogen phosphates, especially those of sodium, moreover, organic and inorganic acids such as, for example, hydrochloric acid, sulphuric acid, phosphoric acid, citric acid, cromoglycinic acid, acetic acid, lactic acid, tartaric acid, succinic acid, fumaric acid, lysine, methionine, acidic hydrogen phosphates of sodium or potassium etc. and further buffer systems as described above. In further specific embodiments, the pharmaceutical compositions for use according to the present invention comprise one or more further excipients which are selected from chelating agents, example, disodium edetate dihydrate, calcium sodium EDTA, preferably disodium edetate dihydrate.

The pharmaceutical compositions for use according to the present invention may be provided in solid form such as in form of a lyophilisate that is suitable for and may be reconstituted in an aqueous carrier liquid. The term "reconstituted" as used herein means that the lyophilized pharmaceutical compositions obtained or generated by the lyophilization process in form of a solid material may be re-dissolved or re-dispersed, preferably re-dispersed in an aqueous carrier liquid.

In specific embodiments, such lyophilized pharmaceutical compositions suitable for the preparation of the pharmaceutical compositions for use according to the present invention may further comprise at least one disaccharide selected from the group consisting of saccharose (sucrose; the terms 'saccharose' and 'sucrose' as used herein have the same meaning and are used synonymously for β-D-fructofuranosyl α-D-glucopyranoside; CAS number 57-50-1), lactose (β-D-galactopyranosyl-(1→4)-D-glucose; CAS number 63-42-3) and trehalose (α-D-glucopyranosyl-(1→1)-α-D-glucopyranoside; CAS number 99-20-7). In further specific embodiments, the at least one disaccharide is present in an amount of at least about 40 wt.-% with regard to the total weight of the lyophilized composition. In some embodiments, the at least one disaccharide is present in an amount of from at least about 40 wt.-% up to about 95 wt.-% or up to about 90 wt.-% or up to about 85 wt.-% or up to about 80 wt.-%, all with regard to the total weight of the lyophilized composition.

In further specific embodiments, the lyophilized compositions suitable for the preparation of the pharmaceutical compositions of the present invention comprise saccharose and/or trehalose, preferably saccharose as the disaccharide which is present in an amount of at least about 40 wt.-% with regard to the total weight of the lyophilized composition. In yet further embodiments, the lyophilized compositions suitable for the preparation of the present pharmaceutical compositions by reconstitution may comprise the at least one disaccharide, preferably saccharose and/or lactose, especially saccharose, in an amount selected in the range of from about 50 wt.-% to about 80 wt.-% or about 75 wt.-%, with regard to or based on the total weight of the lyophilized composition. In further preferred embodiments, the lyophilized pharmaceutical compositions may comprise the at least one disaccharide, preferably saccharose and/or lactose, especially saccharose in an amount selected in the range of from about 60 wt.-% to about 75 wt. %, even more preferably selected in the range of from about 65 wt.-% to about 70 wt.-% with regard to the total weight of the lyophilized composition.

In further specific embodiments, the lyophilized compositions comprising an inhalable immunosuppressive macrocyclic active ingredient in liposomally solubilized form, preferably L-CsA, which are suitable for the preparation of the present pharmaceutical compositions have been prepared in the presence of the at least one disaccharide selected from saccharose, lactose and/or trehalose.

Without wishing to be bound by theory, this may be attributed to the stabilizing effect of the disaccharide selected from the group of saccharose, lactose and trehalose which is preferably present in an amount of at least 40 wt.-%, based on the total weight of the lyophilized pharmaceutical composition. Furthermore, the above-described beneficial properties of the lyophilized pharmaceutical compositions, preferably L-CsA, may be attributed to the fact that the disaccharide selected from the group consisting of saccharose, lactose and trehalose, preferably saccharose, is present on the outside as well in the inner lumen of the liposome-forming structures.

In further embodiments, the lyophilized compositions suitable for the preparation of the present pharmaceutical compositions by reconstitution may comprise CsA in an amount of from about 2 to about 4 wt.-%, preferably of from about 2.2 to about 3.4 wt.-% or even more preferably of from about 2.4 to about 3.4 wt.-% or from about 2.4 wt.-% to about 3.0 wt.-%, based on the weight of the lyophilized composition. In further specific embodiments, in such lyophilized compositions, the ratio of the weight of the at least one disaccharide to the weight of cyclosporine A in the lyophilized composition may be selected in the range of from about 10:1 to about 30:1, or from about 20:1 to about 30:1 or from about 20:1 to about 27.5:1 or even from about 22.5:1 to about 27.5:1.

The lyophilized precursor compositions suitable for the preparation of the present pharmaceutical compositions by reconstitution may be is dissolved or, more specifically, dispersed in an aqueous carrier liquid, preferably in a sterile aqueous carrier liquid. The aqueous carrier liquid may be water or an aqueous solution of pharmaceutically acceptable salts or isotonizing agents and preferably may be sterile. In preferred embodiments, however, the sterile aqueous carrier liquid is an aqueous sodium chloride solution, preferably with the sodium chloride content of all 0.25% (w/v). Furthermore, the sterile aqueous carrier liquid may further comprise one or more buffer agents, preferably as described above. Preferably, the sterile aqueous carrier liquid, especially the aqueous sodium chloride solution has a pH-value in the range of from 4.0 to 7.0 and an osmolality in the range of from about 60 to about 100 mOsmol/kg.

Advantageously, the sterile aqueous carrier liquid is provided in an amount suitable for the preparation of pharmaceutical composition for use according to the present invention in form of an aqueous liposomal dispersion for inhalation comprising CsA or another immunosuppressive macrocyclic active ingredient, e.g. tacrolimus, in liposomally solubilized form. In specific embodiments, the amounts of the lyophilized precursor composition and the aqueous carrier liquid may be chosen in the ranges as exemplarily described above. In further preferred embodiments, the amount of the chosen lyophilized precursor composition comprising at least one disaccharide selected from the group consisting of saccharose, lactose and trehalose, preferably in an amount of at least 40 wt.-% with regard to the total weight of the lyophilized composition, and the amount of the aqueous carrier liquid may be chosen so that the resulting liquid liposomal dispersion has a content of the at least one disaccharide selected from the group consisting of saccharose, lactose and trehalose, preferably saccharose, in the range of from about 5 to about 15 wt.-%, preferably in the range of from about 7.5 to about 12.5 wt.-%, based on the total weight of the resulting pharmaceutical composition for use according to the present invention.

In particularly preferred embodiments, at least one disaccharide selected from the group consisting of saccharose, lactose and trehalose is present in the resulting liquid liposomal dispersion in an amount in the range of from about 5 to about 10 wt.-% or from about 7.5 to about 10 wt.-%, or in an amount of about 7.5 wt.-% or about 10 wt.-%, all based on the total weight of the liquid liposomal dispersion.

In exemplary embodiments, the sterile aqueous carrier liquid, especially the aqueous sodium chloride solution as described above is provided in an amount of about 1.10 mL to about 1.50 mL to be combined with an aliquot of about 185 mg of a lyophilized precursor composition as described in Example 1 containing about 2.7 wt.-% of CsA (corresponding to 5 mg of CsA). In further exemplary embodiments, the sterile aqueous carrier liquid, especially the aqueous sodium chloride solution as described above is provided in an amount of about 2.20 mL to about 2.80 mL to be combined with an aliquot of about 375 mg of the lyophilized precursor composition as described in Example 1 containing about 2.7 wt.-% of CsA (corresponding to 10 mg of CsA).

In specific embodiments, the pharmaceutical compositions for use according to the present invention may be provided in form of a liquid liposomal dispersion comprising an aqueous carrier liquid or vehicle and a therapeutically effective amount of the chosen macrocyclic immunosuppressive active ingredient, preferably CsA, in liposomally solubilized form. In further embodiments, the liquid liposomal dispersion is essentially free from visible particles. The liposomes comprised by said dispersion preferably may have an average diameter or, more specifically, a z-average diameter of at most about 100 nm as measured by photon correlation spectroscopy using a Malvern ZetaSizer. Preferably, the liquid liposomal dispersion comprises liposomes with a z-average diameter as measured by photon correlation spectroscopy (Malvern ZetaSizer) in the range of from about 40 nm to about 100 nm and even more preferably in the range of from about 40 nm to about 70 nm. Such a liquid liposomal dispersion may have a polydispersity index (PI) as measured by photon correlation spectroscopy of up to about 0.50, preferably of up to about 0.4 and even more preferably in the range of from about 0.1 to about 0.3. Furthermore, such liquid liposomal dispersions comprising the chosen macrocyclic immunosuppressive active ingredient, preferably CsA, in liposomally solubilized form may have an osmolality in the range of from about 300 to about 550 mOsmol/kg, preferably in the range of from about 430 to about 550 mOsmol/kg. The pH-value of such liquid liposomal dispersions preferably is in the range of from about 6.0 to 7.0. In further embodiments, after 1:10 dilution the liquid liposomal dispersion according to this aspect of the invention has a turbidity of up to 200 NTU (Nephelometric Turbidity Units).

In exemplary embodiments, the present pharmaceutical compositions for use may comprise the inhalable macrocyclic active ingredient such as tacrolimus or CsA, preferably CsA, in form of a liquid solution, specifically in form of an aqueous liquid solution, or, more specifically in form of a liquid dispersion as described above. In further exemplary embodiments, such liquid compositions may comprise cyclosporine A (CsA) in a concentration in the range of from about 0.2 to about 20 mg/mL, often in an amount from about 1 mg/mL to about 10 mg/mL based on the amount of the final liquid pharmaceutical composition to be nebulized. In case of cyclosporine A, especially in liposomally solubilized form (L-CsA) this active ingredient often is comprised in an amount of about 2 mg/mL to about 8 mg/mL, preferably from about 2 mg/mL to about 6 mg/mL, more preferably from 2.5 mg/mL to about 6 mg/mL, even more preferably from 3 mg/mL to about 4 mg/mL, especially at a concentration of about 4 mg/mL as already described above.

In many cases, the phospholipids or lecithins as described above may be present in the liquid pharmaceutical composition for use according to the present invention in an amount of from about 0.2 to about 15 wt.-% or from about 1 to about 8 wt.-%, based on the total weight of the final composition to be nebulized.

Furthermore, the non-ionic surfactants as described above, preferably the polysorbates such as Tween 80 may be present in the liquid pharmaceutical compositions for use according to the present invention in an amount of from about 0.01 to about 5 wt.-% or from about 0.1 to about 2 wt.-%, based on the total weight of the final composition to be nebulized.

The pharmaceutical composition for use according to the present invention is administered to the subject by inhalation in form of an aerosol as described in further detail below, whereas the aerosol is generated by nebulization or aerosolization of the present pharmaceutical composition. The nebulization or aerosolization of the present pharmaceutical compositions, preferably of the present liquid pharmaceutical compositions is accomplished by using a nebulizer. In preferred embodiments, such a nebulizer is able to convert the present pharmaceutical compositions comprising the macrocyclic immunosuppressive active ingredient such as CsA or tacrolimus in form of a solution, colloidal formulation or suspension, especially when provided in liposomally solubilized form as described above, into a high fraction of droplets which are able to reach the periphery of the lungs.

The nebulizer for the generation of the aerosol comprising the pharmaceutical composition for use according to the present invention comprises as a component a) an aerosol generator comprising a fluid reservoir for holding the pharmaceutical composition or an interface configured to connect a fluid reservoir, and a vibratable membrane having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride.

The aerosol generator according to component a) of the nebulizer useful for the nebulization of the present pharmaceutical compositions may be a so-called membrane aerosol generator comprising a vibratable membrane having a plurality of minute apertures in a central region as described in further detail below. The pharmaceutical composition, specifically the liquid pharmaceutical composition to be nebulized may be applied to one side of the membrane in the central region and the membrane is vibrated by means of a vibrator (such as a piezoelectric element) typically at a frequency in the range of from about 50 to about 300 kHz, more specifically in the range of from about 60 to about 200 kHz, or from about 80 to about 180 kHz or from about 100 to about 140 kHz. Due to the vibration, the liquid pharmaceutical composition applied to one side of the membrane passes the apertures and is nebulized on the opposite side of the membrane. Accordingly, in specific embodiments, the aerosol generator comprises a piezoelectric element (such as a piezoelectric crystal) as a vibration generator.

The vibratable membrane of the aerosol generator may have a convex shape curving towards the aerosol release side of the membrane. In specific embodiments, the vibratable membrane separates the fluid reservoir and the chamber. The vibratable membrane may be made of a metal such as steel or other metals or materials which are compatible with the administration of pharmaceutical compositions such as the compositions for use according to the present invention. In preferred embodiments, however the vibratable membrane comprises or is made of stainless steel.

The vibratable membrane of the aerosol generator has a plurality of apertures through which the pharmaceutical composition for use according to the present invention may be transported and thereby nebulized or aerosolized. The plurality of apertures are adapted to produce an aerosol comprising droplets having a mass median aerodynamic diameter (MMAD) typically in the range of below 5 μm or of up to about 4.0 μm as measured by nebulization of a 0.9% (w/v) aqueous sodium chloride solution. In specific embodiments, the plurality of apertures of the vibratable membrane are adapted to produce an aerosol comprising droplets having a mass median aerodynamic diameter (MMAD) in the range of from about 1.5 μm to about 5.0 μm, such as from about 1.5 μm to about 4.0 μm or from about 2.0 μm to about 4.0 μm or from 2.4 μm to about 4.0 μm as measured by nebulization of a 0.9% (w/v) aqueous sodium chloride solution.

In further specific embodiments, the plurality of apertures are adapted to produce an aerosol comprising droplets having a mass median aerodynamic diameter (MMAD) in the range of from about 1.5 μm to about 3.9 μm, such as from 2.0 μm to about 3.9 μm or from 2.4 μm to about 3.9 μm as measured by nebulization of a 0.9% (w/v) aqueous sodium chloride solution.

In alternative embodiments, the mass median aerodynamic diameter (MMAD) of the droplets generated by the vibratable membrane comprising the plurality of apertures adapted accordingly can be determined by the nebulization or aerosolization of an aqueous solution of liposomally solubilized CsA (L-CsA) with a CsA-concentration of 4.0 mg/mL as described in Example 2.2 below. According to these embodiments, the plurality of apertures are adapted to produce an aerosol comprising droplets having a mass median aerodynamic diameter (MMAD) typically below about 6 μm, such as in the range of from about 2.0 μm to about 5.5 μm, or from 2.5 μm to about 4.5 μm or from about 2.8 μm to about 4.4 μm.

The values for the mass median aerodynamic diameter (MMAD) as referred to herein typically may be associated with a Geometric Standard Deviation (GSD) in the range of up to 2.4, more specifically of up to 2.2 or of up to 2.0 or even of lower than 2.0 such as up to 1.8 or up to 1.7 or, more specifically, may be associated with a Geometric Standard Deviation (GSD) in the range of 1.1 up to 2.4, more specifically of 1.2 up to 2.2 or of 1.3 up to 2.0. In cases in which the GSD value is below 2.0 the corresponding droplet size distribution generated by the aerosol generator or the vibratable membrane, respectively, is referred to as a narrow droplet size distribution or as monodisperse aerosols.

The term 'droplets' as used herein refers to droplets or particles of the aerosolized pharmaceutical composition for use according to the present invention comprising the chosen immunosuppressive macrocyclic active ingredient such as CsA or tacrolimus. In context with the determination of the MMAD of the droplets generated by the vibratable membrane or the plurality of apertures, respectively, the term 'droplets' may also refer to droplets of an 0.9% (w/v) aqueous sodium chloride solution.

The mass median aerodynamic diameter (MMAD) and other metrics of the aerosolized pharmaceutical compositions can be determined by methods known to those of skill in the art by means of e.g. an impactor such as a cascade impactor or by laser diffraction analysis as described e.g. in Eur. Ph. 2.9.44 or to USP chapter <1601>. As a cascade impactor, a multistage cascade impactor may be used such as an 'Anderson Cascade Impactor' (ACI) or preferably a 'Next Generation Impactor' (NGI). These methods allow for the determination of several metrics of the generated aerosol comprising the present pharmaceutical compositions, such as the MMAD as mentioned above, the fine particle dose or fraction (FPD or FPF), the geometric standard deviation (GSD), as well as the respirable dose or fraction (RD or RF).

The use of a multistage cascade impactor such as the ACI or preferably the NGI allows for the characterization of the aerodynamic metrics e.g. generated by the aerosolization/nebulization of a 0.9% (w/v) solution of NaCl as well as for the aerosolization/nebulization of a liquid pharmaceutical composition for use according to the present invention.

The vibratable membrane useful for the nebulization or aerosolization of the present pharmaceutical compositions may typically comprise from about 1000 to about 5000 apertures, or from about 2000 to about 4000 apertures, often from about 1500 to about 3500 apertures. Based on a typical perforated surface area of such a membrane with a diameter less than about 30 $mm^2$, preferably from about 5 $mm^2$ to about 30 $mm^2$, more preferred from about 6 $mm^2$ to about 20 $mm^2$ and even more preferred from about 7 $mm^2$ to about 15 $mm^2$, the vibratable membrane typically may have from about 30 to about 700 apertures per $mm^2$, often from about 60 to about 600 or from about 80 to about 500 or from about 100 to about 400 apertures per $mm^2$ of the perforated surface area.

The mean geometrical diameter of the apertures as measured by scanning electron microscopy (SEM) typically may be up to 4.0 μm or, more specifically in the range of from about 1.5 μm to about 3.0 μm, or from about 1.6 μm to about 2.8 μm or from about 1.8 μm to about 2.6 μm with a standard deviation of typically +/−0.4 μm or more specifically of +/−0.3 μm or even+/−0.2 μm.

In specific embodiments, the plurality of apertures of the vibratable membrane or, more specifically, each aperture of the plurality of apertures may have a tapered shape narrowing towards the aerosol release side of the vibratable membrane. Accordingly, the aperture may be formed as a channel which continuously or discontinuously narrows towards the aerosol release side of the vibratable membrane. In further specific embodiments, the apertures or a single aperture of the plurality of apertures of the vibratable membrane, accordingly, may have an exit diameter corresponding to the minimal mean geometrical diameter of the apertures as described above.

The aerosol generator further comprises a fluid reservoir for holding the pharmaceutical composition for use according to the present invention or an interface configured to connect a fluid reservoir holding the pharmaceutical composition for use according to the present invention. In specific embodiments, the aerosol generator further comprises a fluid reservoir for holding the pharmaceutical composition for use according to the present invention. Through the fluid reservoir a liquid such as specifically the liquid pharmaceutical composition for use according to the present invention may be applied to one side of the central region of the vibratable membrane containing the plurality of apertures. The fluid reservoir may be closed by a lid and typically may have a volume of from about 1 mL to about 10 mL.

The nebulizer for the generation of the aerosol comprising the pharmaceutical composition for use according to the present invention further comprises as a component b) a chamber for temporarily accommodating the aerosol generated by the aerosol generator, the chamber having an inner lumen with a volume in the range of from about 50 to about 150 mL. In specific embodiments, the inner lumen of the chamber may have a volume of more than 60 mL and preferred more than 90 mL such as in the range of from about 70 to about 130 mL or in the range of from about 75 to about 125 ml or more specifically in the range of from about 80 to about 120 mL and even more specifically in the range of from about 90 to about 110 mL or to about 100 mL.

Furthermore, the nebulizer for the generation of the aerosol comprising the pharmaceutical composition for use according to the present invention comprises as a component c) a mouthpiece for delivering the aerosol supplied by the nebulizer to the subject, the mouthpiece having an exhalation filter.

The mouthpiece allows for delivering the pharmaceutical compositions for use according to the present invention supplied by the nebulizer to the subject to be treated and may be attached to the nebulizer. According to an aspect, the mouthpiece may comprise a body defining a fluid path from an inlet port connectable to the nebulizer to an inhalation opening to be received in the mouth of the patient. Moreover, the mouthpiece also has an exhalation filter which may or may not be integrated into the mouthpiece. In particular embodiments, the filter may have a filter base in fluid communication with the fluid path, a filter top detachably connected to the filter base and a filter material provided between the filter base and the filter top. The filter top may have an exhalation opening cooperating with a one-way valve allowing exhaustion of fluid from the fluid path through the filter material to the outside of the mouthpiece upon exhalation of a patient through the inhalation opening. In one embodiment, the one-way valve may be configured by a circular disk made of a flexible material such as silicone or thermoplastic elastomer (TPE), covering the exhalation opening on a side opposite to the filter material. Accordingly, in this embodiment the disk is pushed away from the valve seat (such as ribs crossing (spanning) the exhalation opening) during exhalation so that air may escape from the mouthpiece. To the contrary, the disk is sucked and consequently pressed against the valve seat during inhalation so that no air may enter the mouthpiece during inhalation.

In some embodiments, the filter may be integrated into the mouthpiece. In further embodiments, the body of the mouthpiece and the filter base may be an integrated one-piece unit. To put it differently, in these embodiments, the body of the mouthpiece and the filter base are one element and are not detachable from each other. Due to this configuration, the tube connecting the body and the filter may be kept as short as possible. Therefore, the overall height of the mouthpiece can be reduced so that the filter does not form a visual obstruction for the user enabling him/her to e.g. read and watch television. In addition, the number of parts is significantly reduced as compared to the configuration as described with respect to FIGS. 1 and 2, now consisting of three parts only, the integrated one-piece unit consisting of the body and the filter base, the filter material and the filter top. In addition, the length may be reduced, whereby dead spaces are minimized.

In a particular embodiment, the integrated one-piece unit is an injection molded part. Thus, the mouthpiece may be cost efficiently manufactured.

In addition, the overall length may be reduced in a mouthpiece as described above, whereby dead spaces are minimized. According to an aspect, this is assisted in that a distance between the center line of the filter base and the inhalation opening of the mouthpiece as seen in a side view is at least 30 mm or in another aspect at least 35 mm, but not more than 50 mm, in another aspect not more than 40 mm. Thus, it may be ensured that there is still enough space between the filter base and the inhalation opening to accommodate the nose of a user without the nose touching the filter base but that the overall length of the mouthpiece is minimized.

The integration of the filter base into the body of the mouthpiece to form the integrated one-piece unit according to the embodiments as described above enables a reduction in the overall height of the mouthpiece to avoid a visual obstruction for the user during inhalation (see above). According to one aspect, the height of the mouthpiece as seen in a side view is not more than 90 mm, and according to another aspect not more than 85 mm, and in one particular embodiment less than 82 mm. For example, the maximum height may be 81.5 mm.

In one particular aspect, a retaining rib of the mouthpiece for being engaged behind the teeth of a user is provided on an upper side of the body and/or on a lower side of the body adjacent to the inhalation opening. Such a retaining rib facilitates hands free use of the nebulizer.

In order to even ergonomically improve the mouthpiece, one aspect suggests a front edge of the body surrounding the inhalation opening which is curved in a plan view and/or a side view. Thus, the inhalation opening is shaped like the mouth of a fish.

Moreover and according to one aspect, the inlet port may be conical to be force-fittingly connectable to a boss of the nebulizer (similar to a Luer taper or Luer Lock system). Such a configuration of the interface between the mouthpiece and the nebulizer in principle allows any orientation of the mouthpiece relative to the nebulizer, e.g. with the filter directed upward, downward, towards the sides or tilted. In combination with integrated one-piece unit, the orientation of the mouthpiece at the nebulizer may be advantageously determined by the configuration of the filter base and/or the configuration of the inhalation port of the mouthpiece despite this general possibility. For example, the filter base may be configured to interfere with the chamber of the nebulizer when the mouthpiece is rotated about the boss of the nebulizer preventing or limiting such rotation.

In another example, the inhalation opening may be oval-shaped in a front view, the oval shape having a minor axis and a major axis, wherein the filter base (and/or the tube connecting the body and the filter base) extends from the body in a direction along the minor axis. Thus, only an orientation in which the filter is directed upward (or downward) is allowed.

In one aspect, the aerosol generator, the chamber and the mouthpiece may be arranged in that order along the longitudinal direction of the nebulizer. Thus, the nebulizer as such is already relatively long. Yet, by reducing the overall length of the mouthpiece along the longitudinal direction as described above, the overall length of the nebulizer may be minimized. Accordingly, the lever arm when holding the nebulizer with the teeth at the inhalation opening of the mouthpiece may be reduced facilitating hands-free inhalation.

According to a further aspect, the nebulizer further comprises a fluid reservoir or an interface configured to connect a fluid reservoir as described above, wherein the aerosol generator comprises a vibratable membrane having a plurality of apertures (see above) and separating the fluid reservoir and the chamber.

According to a further aspect, the fluid reservoir or the interface and the membrane are arranged in that order along the longitudinal direction of the nebulizer. When the fluid reservoir or the interface and the membrane are arranged in that order along the longitudinal direction of the nebulizer, the general length of the nebulizer is increased. Yet, it is possible to shorten the mouthpiece by integrating the filter base into the mouthpiece as explained above so that the overall length of the nebulizer can be minimized.

Similar applies to the case in which the chamber has a length ($L_C$) along the longitudinal direction of the nebulizer between 30 mm and 100 mm, particularly 50 mm to 100 mm and more particularly not less than 70 mm, such as not less than 80 mm or not less than 90 mm. Again, the use of such a chamber which is beneficial for providing a sufficiently large bolus in the chamber which is to be inhaled by the user lengthens the nebulizer and, hence, the lever arm when the nebulizer is held by the teeth at the inhalation opening of the mouthpiece. Due to the possibility to shorten the mouthpiece including the filter this lever arm may again be reduced in length or minimized.

According to one aspect, the chamber has an ambient opening cooperating with a one-way valve allowing ambient air to enter the chamber from outside of the nebulizer upon inhalation of a patient through the inhalation opening of the mouthpiece.

As previously indicated, the mouthpiece and the nebulizer described herein are useful for the administration or nebulization/aerosolization of the pharmaceutical compositions for use according to the present invention comprising an inhalable immunosuppressive macrocyclic active ingredient such as tacrolimus or cyclosporine A, especially cyclosporine A (CsA).

Further features and aspects of the invention, particularly of the nebulizer and mouthpiece useful for the administration of the pharmaceutical compositions for use according to the present invention are described in further detail below with respect to particular examples making reference to the accompanying drawings. In the several drawings, the same reference numerals have been used for the same and the like elements.

DETAILED DESCRIPTION OF THE DRAWINGS

Figure 2:
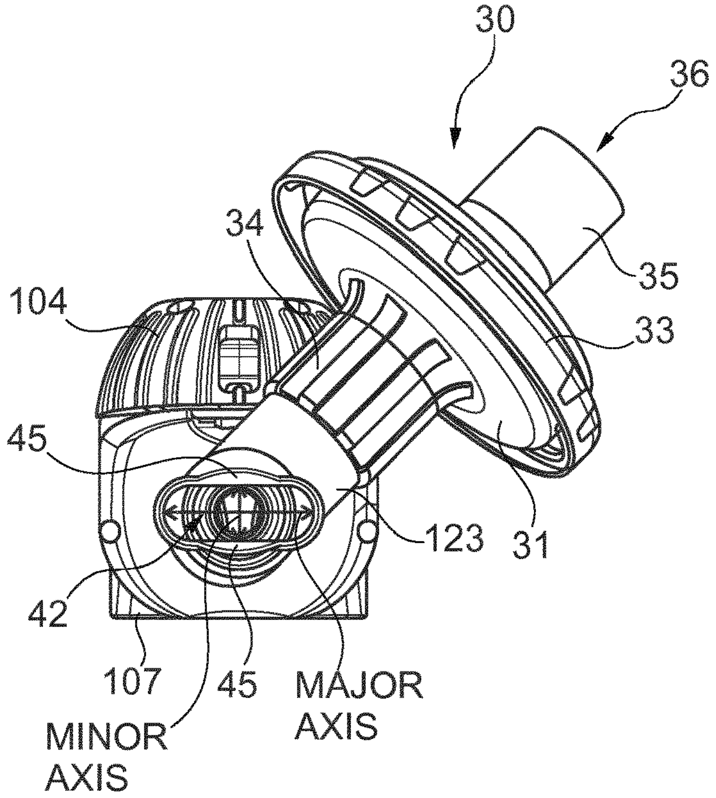
FIG. 2 shows a perspective front view on the nebulizer of FIG. 1, but with the filter being tilted to the right.

FIGS. 1 and 2 show a nebulizer 100 of a predevelopment similar to the one described in EP 1 927 373 B1. So as to provide an exhalation filter 30, it had first been conceived to connect a T-shaped adapter 120 at a connection port 121 to a chamber 105 of the nebulizer 100 for temporarily accommodating the aerosol generated by the aerosol generator 101 (see FIG. 5). A mouthpiece 40 is connected to the adapter 120 at a boss 122 opposite to the connection port 121. Moreover, an exhalation filter 30 comprising a filter base 31, a filter top 33 detachably connected to the filter base 31 and a filter material 32 provided between the filter base 31 and the filter top 33 is provided. The filter base 31 is connected to a filter connection port 123 of the adapter 120 located between the connection port 121 and the boss 122.

This approach has however been conceived disadvantageous for several reasons. First of all, if the filter is directed upward (not shown), the filter is positioned closely in front of the user's nose and eyes. This is due to its height perceived uncomfortable, particularly if the user intends to read or watch television during inhalation.

The attempt to rotate the filter to the right (alternatively to the left) as shown in FIG. 1 or so as to be directed downward leads to the problem that the nebulizer may no longer be placed on a horizontal surface because of the dimensions of the filter interfering with the horizontal surface. Positioning the filter in a tilted position, as shown in FIG. 2, leads to instability of the nebulizer when being placed on a horizontal surface. Thus, handling of the nebulizer is impaired. Even further, this configuration employs a plurality of parts, namely the T-shaped adapter, the filter base, the filter material, the filter top and the mouthpiece (5 parts in total). This is perceived disadvantageous in handling the nebulizer as it needs to be disassembled for cleaning and subsequently again be assembled for use. Moreover, this configuration significantly increases the overall length $L_0$ of the nebulizer. However, such nebulizers are often used hands free by holding the nebulizer at the inhalation opening of the mouthpiece by means of the teeth. Yet, the longer the nebulizer is, the longer is the lever arm and the more difficult it is to use the nebulizer hands free. The same holds true if the filter is positioned in the tilted position as shown in FIG. 2 and if rotated to one side as shown in FIG. 1. These positions induce a rotational force on the teeth which is perceived uncomfortable.

Finally, this configuration leads to an increased dead space from the connection port 121 to the inhalation opening 42 at the mouthpiece 40 in which the aerosol may deposit and be washed out onto the filter during exhalation and, thus, be wasted.

In specific embodiments, the mouthpiece 40 according to component c) of the aerosol generator 100 comprises:

a body 46 defining a fluid path 47 from an inlet port 41 connectable to the nebulizer 100 to an inhalation opening 42 to be received in the mouth of the user; and an exhalation filter 30 having a filter base 31 in fluid communication with the fluid path 47, a filter top 33 detachably connected to the filter base and a filter material 32 provided between the filter base and the filter top, wherein the filter top has an exhalation opening 36 cooperating with a one-way valve 39 allowing exhaustion of fluid from the fluid path through the filter material to the outside of the mouthpiece upon exhalation of a patient through the inhalation opening; wherein the body and the filter base are an integrated one-piece unit.

The drawings show a nebulizer 100 comprising an aerosol generator 101 (see FIG. 5) and a chamber 105 for temporarily accommodating the aerosol generated by the aerosol generator. In the example, the aerosol generator 100 comprises a vibratable membrane 110 having a plurality of apertures in a central region 111. Moreover, a piezoelectric ring 112 is provided to vibrate the membrane 110.

Figure 5:
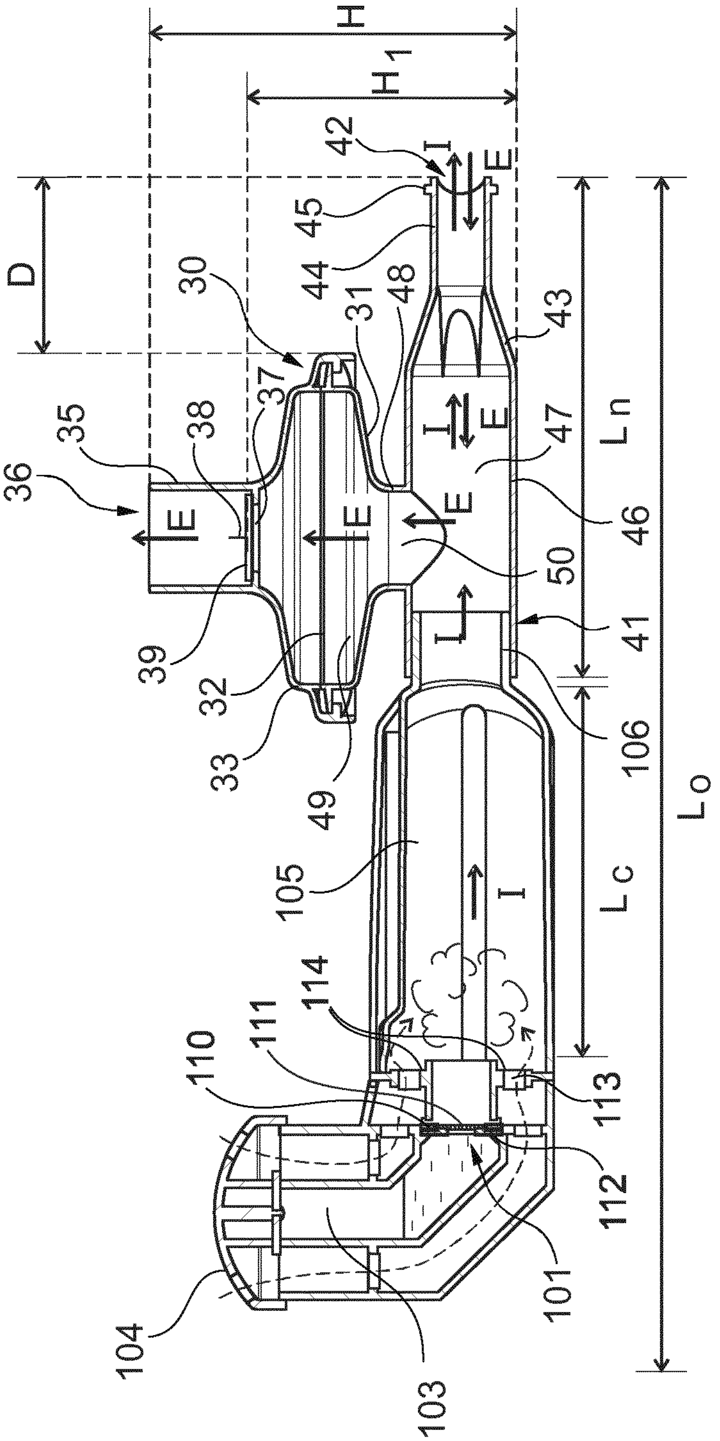
FIG. 5 shows a longitudinal sectional view of the nebulizer and the mouthpiece of FIGS. 3 and 4.

In addition, the nebulizer 100 comprises a fluid reservoir 103 applying a liquid (such as a liquid pharmaceutical composition for use according to the present invention) to one side of the central region 111 of the membrane 110 containing the apertures (see FIG. 5). The fluid reservoir 103 is closed by a lid 104. In general, such a nebulizer is disclosed in EP 1 927 373 B1 and EP 1 353 759 B1. Instead of a fluid reservoir it is also conceivable to provide an interface such as a needle or collar configured to connect a fluid reservoir such as an ampoule. Such system is for example disclosed in EP 1 919 542 B1.

In use, a liquid or fluid, or more specifically the pharmaceutical compositions for use according to the present invention, may be applied to the one side of the membrane 110 (aerosol generator) and is passed through the apertures by vibrating the membrane via the piezoelectric element 112 whereby the aerosol is introduced (ejected) into the chamber 105. Thus, the membrane 110 (aerosol generator) is disposed between the fluid reservoir 103 and the chamber 105. The chamber 105 is configured for temporarily accommodating the aerosol generated by the membrane 110 as a bolus to be inhaled by the subject or patient.

A longitudinal end of the chamber 105 opposite to the end at which the membrane 110 is disposed comprises a boss 106 defining a discharge opening and being circular in cross section. The boss 106 may be cylindrical or tapered resembling a male taper similar to a Luer taper System.

Further, the chamber 105 resembles a stand enabling to place the nebulizer 100 on a horizontal surface such as a table.

In addition, ambient openings 113 are disposed at one end of the chamber 105 close to the aerosol generator 101. These openings 113 cooperate with a one-way valve 114 such as flaps or reed valves allowing ambient air to enter the chamber 105 upon inhalation of a patient.

If the nebulizer 100 is to be used with a liquid or fluid, such as a liquid pharmaceutical composition for use according to the present invention containing a compound that may be detrimental to individuals staying in the environment in which the user inhales, there is a need to implement an exhalation filter 30.

In the predevelopment it was conceived to use a T-shaped adapter 120 to attach the exhalation filter 30. The T-shaped adapter 120 comprises an inlet port 121 being circular in cross section. The inlet port 121 is cylindrically shaped or tapered resembling a female taper similar to a Luer taper. The T-shaped adapter 120 is connected by force fit with its inlet port 121 to the boss 106.

An outlet port 122 is disposed opposite to the inlet port 121. The outlet port 122 is configured similar to the boss 106 and is, hence, also circular in cross section and may be cylindrically shaped or tapered resembling a male taper of a Luer taper System.

A filter connection port 123 is disposed at an intermediate position between the inlet port 121 and the outlet port 122 and extends substantially perpendicular to a direction from the inlet port 121 to the outlet port 122 defining the T-shape. The filter connection port 123 is circular in cross section and may be cylindrically shaped or tapered resembling a male taper of a Luer taper System.

The exhalation filter 30 comprises a filter base 31, a filter material 32 (see FIGS. 4 and 5) and a filter top 33. The filter base 31 comprises a connecting tube 34 which is circular in cross section and may either be cylindrically shaped or tapered resembling a female Luer taper. Accordingly, the exhalation filter 30 may be connected to the filter connecting port 123 by force fit.

The filter material 32 may be made of polypropylene or the like. In one example, the filter may be made of blended synthetic fibers for example attached to polypropylene spun bonded scrim. The filter may typically have a thickness of between 1.5 mm to 5.5 mm or 2 mm to 5 mm or about 3.5 mmm. The air permeability at 200 Pa may be from about 400 to about 600 $L/m^2s$ and/or an air flow resistance may be about 46.0 PA at a medium velocity of 9.5 m/min. An exemplary filter is Microstat+250 MED sold by Riensch & Held, Germany. The filter material 32 is sandwiched between the filter base 31 and the filter top 33 as will be apparent from FIG. 5. Thus, the filter base 31 of the filter top 33 form a compartment accommodating the filter material 32.

The filter top 33 is detachably mounted to the filter base 31 using for example a snap fit. The filter material may be changed by detaching the filter top 33 from the filter base 31.

Moreover, the filter top may comprise another boss 35 allowing connecting a tube or other equipment. Yet, this boss 35 may as well be omitted for example to reduce the device height.

Further, an exhalation opening 36 is provided in the filter top 33. The exhalation opening 36 may be circular in cross section. In one aspect, a plurality of radial ribs 37 (FIG. 5) extend across the exhalation opening 36 and a pin 38 is formed in a center thereof. A one-way valve 39 (in the present aspect a disk made of a flexible material) is fixed to the pin 38 so as to be disposed on a side of the ribs 37 opposite to the compartment and the filter material 32. Thus, the one-way valve 39 allows fluid to flow from the compartment between the filter base 31 and the filter top 33 valve 39 opens (the disc 39 lifts from the radial ribs 37 allowing the fluid to pass between the ribs 37 through the exhalation opening 36 to the outside). However, the valve 39 blocks the flow of fluid in the opposite direction from the environment toward the compartment in that it closes (the disc 39 is pressed against the radial ribs 37 closing the openings between the ribs 37 and hence blocking the exhalation opening 36).

Moreover, FIGS. 1 and 2 show a mouthpiece 40 having a connecting portion 41 circular in cross section and cylindrically shaped or tapered resembling a female Luer taper, like a tube connector used in intensive care units. The connecting portion 41 is connected to the outlet port 122 of the T-shaped adapter 120 by force fit. This may provide an airtight seal at the connection between the connecting port 41 and the T-shaped adapter 120.

An inhalation opening 42 may be provided opposite to the connecting portion 41. The inhalation opening 42 is oval in cross section as best visible from FIG. 2. Thus, the inhalation opening 42 comprises a major axis substantially oriented horizontally and/or parallel to the stand 107 and a minor axis extending perpendicularly to the major axis.

In this context, the mouthpiece 40 contains a taper 43 in which the mouthpiece 40 changes its cross section from a circular cross-section at the connecting portion 41 to the oval cross-section of the inhalation opening 42. Thus, the mouthpiece 40 tapers at an intermediate position 43 defining a substantially flat portion 44 to be accommodated in the mouth of a subject or patient.

Further, retaining ribs 45 are formed on the long sides of the oval cross-section adjacent the inhalation opening 42 extending substantially perpendicular from the portion 44.

Thus, the teeth may catch or engage behind the retaining ribs 45 and the user may hold the entire nebulizer with his/her teeth and use it hands free.

This predevelopment, even though providing the required function of filtering exhausted air, has, however, disadvantages. For example, if the filter 30 is directed upward (not shown), the filter is positioned closely in front of the user's nose and eyes. In other words, the height H of the nebulizer is too large. This is perceived uncomfortable, particularly if the user intends to read or watch television during inhalation. The attempt to rotate the filter to the right (alternatively to the left) as shown in FIG. 1 or so as to be directed downward leads to the problem that the nebulizer may no longer be placed on a horizontal surface in view of the stand 107 because of the dimensions of the filter. Positioning the filter in a tilted position, as shown in FIG. 2, leads to instability of the nebulizer when being placed on a horizontal surface. In particular in this configuration, the nebulizer would tend to tilt over. Thus, handling of the nebulizer is impaired.

Even further, this configuration employs a plurality of parts, namely the T-shaped adapter 120, the filter base 31, the filter material 32, the filter top 33 and the mouthpiece (making in total 5 parts). This is perceived disadvantageous in handling the nebulizer as it needs to be disassembled for cleaning and subsequently again be assembled for use and may lead to an inaccurate assembly of parts and to misuse without filter and exhalation valve.

Moreover, this configuration significantly increases the overall length $L_0$ of the nebulizer. However, such nebulizers are often used hands free as explained above by holding the nebulizer at the inhalation opening of the mouthpiece using the retaining ribs by means of the teeth. Yet, the longer the nebulizer is, the longer is the lever arm and the more difficult it is to use the nebulizer hands free. This effect is even more severe when a relatively long mixing chamber 105 having a length $L_C$ between 80 mm and 100 mm is used.

Finally, this configuration leads to an increased dead space from the connection port 121 to the inhalation opening 42 at the mouthpiece 40 in which the aerosol may deposit and be washed out onto the filter 32 during exhalation, thus, be wasted.

Figure 3:
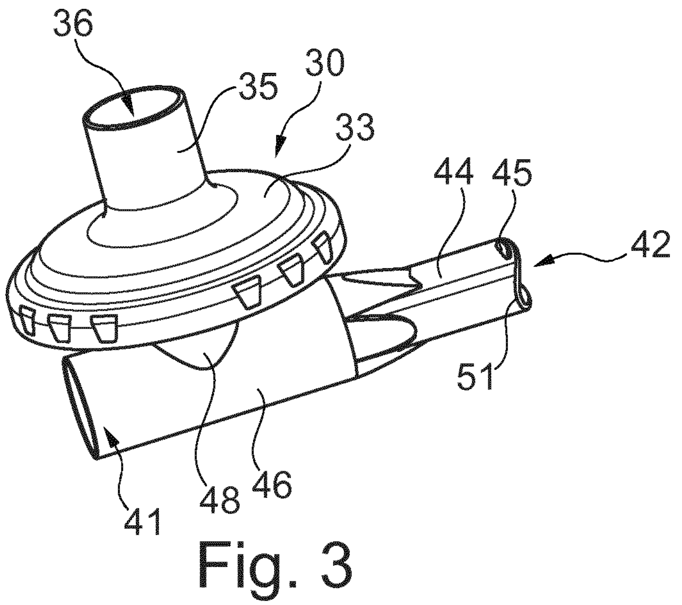
FIG. 3 shows a perspective side view of a mouthpiece for the nebulizer according to FIG. 1.
Figure 4:
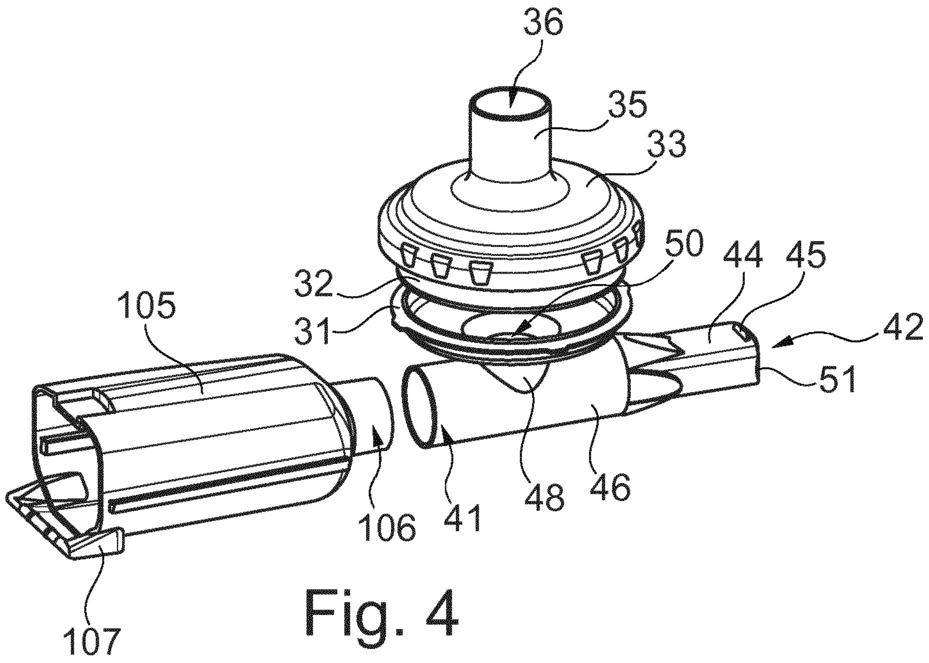
FIG. 4 shows an exploded view of the mouthpiece of FIG. 3 and a nebulizer mixing chamber.

Most of these problems may be alleviated in particular, when the adapter 120 and the filter base 31 have been integrated into the mouthpiece 40 as particularly shown in FIGS. 3 to 5 as one-piece unit with a defined connector to the chamber 105.

Thus, the mouthpiece 40 according to an aspect comprises a body 46 having the inlet port 41 resembling the connection port 121 of the adapter 120. The inlet port 41 is, thus, connectable to the boss 106 of the chamber 105 of the nebulizer 100 by force fit.

The body 46 defines a fluid path 47 from the inlet port 41 to the inhalation opening 42.

In addition, in the embodiments as shown in FIGS. 3 to 5 the filter base 31 is integrally formed with the body 46. In particular, the body 126 comprises a nipple 48 perpendicularly extending from the body 46 in a direction of the minor axis of the inhalation opening 42. The nipple 48 resembles the filter connection boss 123 and connection port 35. Thus, the body together with the exhalation filter 30 forms a further fluid path 49 from an opening 50 opening into the fluid path 47 through the exhalation filter 30 passing the filter material 32 and exiting through the exhalation opening 36.

Thus, according to this preferred embodiment, the filter base 31, the nipple 48 and the body 46 including the inhalation opening 42 and the connection port 41 define an integrated one-piece unit. In one aspect, this integrated one-piece unit is formed by injection molding. Accordingly, in this embodiment the integrated one-piece unit of the body (46) and the filter base (31) are an integrated one-piece unit is an injection molded part.

The filter material 32 and the filter top 33 may remain the same as previously described. Similar applies to the configuration of the mouthpiece with respect to the inhalation opening 42, the ribs 45, the tapering 43 and the portion 44.

However, and in order to even further improve the ergonomic shape of the mouthpiece 40 adjacent to the inhalation opening 42, the edge 51 bordering the inhalation opening 42 is shaped similar to the mouth of a fish. To put it differently, the edge is curved inwardly in a side view and outwardly in a top view as best visible from FIG. 3.

In a further embodiment, the opening 42 may have at least two ribs juxtaposed to each other in the longitudinal direction L to ensure a better hold with the teeth.

In use, a liquid, namely the pharmaceutical composition for use according to the present invention, is nebulized by the aerosol generator 101 into the chamber 105 were the aerosol is temporarily stored. Upon inhalation of a user through the inhalation opening 42, ambient air flows through the openings 113, wherein the valves 114 open into the chamber 105 and entrains the aerosol, which flows from the chamber 105 through the boss 106 and the connection port 41 through the fluid path 47 and is inhaled through the inhalation opening 42 as indicated by the arrows I in FIG. 5. During inhalation, the disk 39 closes the openings between the radial ribs 37 and, hence, the exhalation opening 36 so that no ambient air may enter through the exhalation opening 36.

Upon exhalation, the exhaled air from the patient or user is introduced through the inhalation opening 42 and flows through the fluid paths 47 and 49 as indicated by the arrow E in FIG. 5 through the opening 50 into the exhalation filter 30 passes the filter material 32 and exits the inhalation filter 30 through the exhalation opening 36. During this process, the disk 39 lifts from the radial ribs 37 and allows the exhaled and filtered air to pass and exit through the exhalation opening 36. During this process, the valves 14 close the openings 113 so that the only possibility for the exhaled air to escape is through the filter 30. Especially fluids that are partly toxic should be avoided to be set out to the environment for assistant persons.

Due to the preferred integration of the filter base 31 and the adapter 120 into the mouthpiece 40, particularly into the body 46 thereof, the length $L_M$ of the mouthpiece 40 can be kept short as compared to the length of the adapter 120 and the mouthpiece 40 shown in FIGS. 1 and 2. Accordingly, the overall length $L_O$ of the nebulizer 100 can be reduced. As a result, the lever arm can be shortened and it is easier to use the nebulizer 100 free-hand by retaining the nebulizer 100 via the teeth engaging with the retaining ribs 45 and thereby support the nebulizer 100.

The preferred setup as a one-pieced unit, of the filter base 31, the nipple 48 and the body 46 including the inhalation opening 42 and the connection port 41, ensures that the entire exhaled air including the generated aerosol is filtered before the aerosol is exhausted from the device.

In addition, by keeping a distance D between the filter base 131 and inhalation opening 42 as seen in the side view (FIG. 5) between 30 and 50 millimeters, preferably between 35 millimeters and 40 millimeters, there is sufficient space to accommodate the nose of a user without the nose touching the inhalation filter 30 at the same time reducing the overall length $L_M$ of the mouthpiece 42 to its minimum.

In addition, because of the incorporation of the filter connecting port 123 and the connecting tube 34 into the body 46, the filter base 31 may be brought closer to the body 46 whereby the overall height H in side view may be reduced to not more than 90 mm. In the shown example, the maximum height H is 81.5 mm. When omitting the boss 35, the height may even be further reduced to the height $H_1$. The overall height from the filter base to the exhalation filter opening of the mouthpiece will be further reduced. As one aspect, the height of the mouthpiece as seen in a side view (FIG. 5) is not more than 75 mm, and according to another aspect not more than 70 mm, and in one particular embodiment less than 57 mm. For example, the maximum height may be 56.2 mm.

As a result, the suggested aspects according to this embodiment provide significant advantages particularly as compared to the internal predevelopment as described above.

The inlet port 41 has been described above as forming a female taper of a Luer taper (the boss 106) cooperating with a male taper (the boss 106). Yet, the inlet port 41 may as well be configured as a male taper of a Luer taper cooperating with a female taper at the chamber 105.

LIST OF REFERENCE NUMERALS

30 exhalation filter
31 filter base
32 filter material
33 filter top
34 connecting tube
35 connecting port
36 exhalation opening
37 radial ribs
38 pin
39 one-way valve
40 mouthpiece
41 inlet port
42 inhalation opening
43 tapering
44 flat portion
45 retaining rib
46 body of mouthpiece
47 fluid path
48 nipple
49 further fluid path
50 opening of further fluid path
51 front edge of the body
100 nebulizer
101 aerosol generator
103 fluid reservoir
104 lid
105 chamber
106 boss (of the nebulizer)
107 stand
110 vibratable membrane
111 central region of the membrane
112 piezoelectric element
113 ambient opening
114 one-way valve
120 T-shaped adapter
121 connection port
122 boss
123 filter connection port The nebulizer and mouthpiece as described in detail above allows for the administration of the pharmaceutical compositions for use according to the present invention. Especially when provided in form of a solution, colloidal formulation or suspension, the nebulizer and mouthpiece allow for generating the aerosol comprising the present pharmaceutical compositions to be administered in a high fraction of droplets or particles which are able to reach the periphery of the lungs ("Fine Particle Fraction"; FPF). In specific embodiments, these droplets or particles have a mass average particle diameter of equal or lower than 5 μm as measured e.g. by laser diffraction using a Malvern MasterSizer X or using a multistage cascade impactor such as the Anderson Cascade Impactor (ACI) or the Next Generation Impactor (NGI).

In specific embodiments of the pharmaceutical composition for use according to the present invention, the aerosol to be administered to the patient comprises droplets wherein at least 50%, more specifically from about 60 to about 95% or more specifically from about 70% to about 90% of the total number of droplets have a diameter of up to 5 μm (as measured by laser diffraction or by a multistage cascade impactor as described above) when measured with a aqueous composition comprising L-CsA in a concentration of 4 mg/mL as described in Example 2.2 below.

The nebulizer and mouthpiece as described in detail above further allow for the administration of the pharmaceutical compositions for use according to the present invention with a higher percentage of drug available as delivered dose (DD) and respirable dose (RD) compared to conventional nebulizers such as jet nebulizers. The term 'delivered dose' (DD) as used herein means the fraction of the active ingredient filled into the nebulizer for aerosolization and inhalation which is actually delivered to the targeted tissue, in case of the present invention to the lungs or, more specifically to the peripheral tissues of the lung. Accordingly, in specific embodiments of the present invention, the inhalable immunosuppressive macrocyclic active ingredient, preferably cyclosporine A (CsA) is delivered to the lungs (or the lung) of the subject in an amount of at least 60% or even at least 70%, more specifically in an amount in the range of from about 70% to about 80% of the amount administered to the subject.

Furthermore, the nebulizer and mouthpiece as described above allow for the administration of the pharmaceutical compositions for use at a high total output rate (TOR) which is typically above about 150 mg/min corresponding to about 0.15 mL/min for liquid compositions with a relative density of about 1, with regard to the final pharmaceutical composition to be nebulized and administered. In specific embodiments, the inhalable immunosuppressive macrocyclic active ingredient is administered to the subject at a total output rate (TOR) of at least 200 mg/min or more specifically at a total output rate in the range of from about 200 mg/min to about 300 mg/min or of from about 200 to about 250 mg/min. Accordingly, the nebulizer and mouthpiece as described above allows for a short nebulization time of the present liquid pharmaceutical composition. Obviously, the nebulization time will depend on the volume of the composition which is to be aerosolized and on the output rate.

The volume of a unit dose of the pharmaceutical compositions for use according to the present invention is preferably low in order to allow short nebulization times. The volume, also referred to as the volume of a dose, or a dose unit volume, or a unit dose volume, should be understood as the volume of the pharmaceutical composition to be aerosolized or nebulized which is intended for being used for one single administration. A unit dose is defined as the dose of cyclosporine A in the formulation filled in the nebulizer for one single administration. Specifically, the volume of a unit dose may be less than 10 mL or less. Preferably, the dose unit volume is in the range from about 0.3 to about 3.5 mL, more preferably about 1 to about 3 mL. For example, the volume is about 1.25 mL or about 2.5 mL. In case the formulation is obtained after reconstitution, the volume of the saline solution for reconstitution should be adapted according to the desired volume of the reconstituted formulation.

The unit dose of the macrocyclic immunosuppressive active ingredient, preferably CsA typically is within the range of from about 1 mg to about 15 mg. In specific embodiments, a unit dose of the chosen active ingredient, preferably CsA is about 5 mg or about 10 mg.

Accordingly, in specific embodiments, 1 mL of the pharmaceutical composition comprising an inhalable immunosuppressive macrocyclic active ingredient is aerosolized (nebulized) within a period of up to about 5 min, preferably of up to about 4 min, specifically in cases in which a liquid aqueous composition comprising CsA in liposomally solubilized form at a concentration of 4 mg/mL is administered.

In addition to providing a high delivered dose and having short nebulization times, the nebulizer and mouthpiece for administering the present pharmaceutical compositions is constructed in such way that contamination of the environment with the immunosuppressive macrocyclic active ingredient such as CsA or tacrolimus is prevented by the exhalation filter of the mouthpiece. Such exhalation filter may reduce or avoid emission of the exhaled amount of the macrocyclic immunosuppressive active ingredient such as CsA or tacrolimus to the environment. However, due to the high percentage of the droplets of the aerosol actually delivered to the targeted tissue as described above, the nebulizer and mouthpiece to be used in connection with the present invention allows for the significant reduction of the exhaled active ingredient. Accordingly, in specific embodiments of the present invention the amount of the inhalable immunosuppressive macrocyclic active ingredient exhaled by the subject is up to 10%, more specifically from about 4% to about 8% of the total amount of active ingredient filled into the nebulizer during standardized simulated breathing, which measure the amount, which is normally administered to the subject and could be collected on the exhalation filter.

Accordingly, in a specific embodiment, the present invention provides for a pharmaceutical composition comprising an inhalable immunosuppressive macrocyclic active ingredient, specifically cyclosporine A, for use in the prevention or treatment of a pulmonary disease or condition in a subject, wherein the pharmaceutical composition is administered to the subject by inhalation in form of an aerosol, and wherein the aerosol is generated by nebulization of the pharmaceutical composition using a nebulizer (100), the nebulizer comprising:

a) an aerosol generator (101) comprising:
   a fluid reservoir (103) for holding the pharmaceutical composition or an interface configured to connect a fluid reservoir, and
   a vibratable membrane (110) having a plurality of apertures, the apertures being adapted to produce an aerosol comprising droplets having a mass median aerodynamic diameter (MMAD) of up to about 4.0 µm as measured with a 0.9% (w/v) aqueous solution of sodium chloride;

b) a chamber (105) for temporarily accommodating the aerosol generated by the aerosol generator (101), the chamber having an inner lumen with a volume in the range of from about 50 to about 150 ml; and c) a mouthpiece (40) for delivering the aerosol supplied by the nebulizer (100) to the subject, the mouthpiece having an exhalation filter (30), wherein the inhalable immunosuppressive macrocyclic active ingredient is administered to the subject at a total output rate (TOR) of at least 200 mg/min and preferably wherein the amount of the inhalable immunosuppressive macrocyclic active ingredient exhaled by the subject is up to 10%, more specifically from about 4% to about 8% of the total amount of active ingredient filled into the nebulizer (during standardized simulated breathing).

It should be understood that these specific embodiments also, as all other embodiments may be combined with other features, embodiments and/or aspects as disclosed herein in connection with, for example, the pharmaceutical composition and/or the inhalable macrocyclic immunosuppressive active ingredient to be administered as described in detail above, and/or in connection with the nebulizer and the mouthpiece as described herein. Furthermore, these embodiments may or may not be combined with specific features of the administration of the pharmaceutical composition such as, for example, with the specific embodiment in which 1 mL of the pharmaceutical composition comprising an inhalable immunosuppressive macrocyclic active ingredient is aerosolized (nebulized) within a period of up to about 5 min, preferably of up to about 4 min, specifically in cases in which a liquid aqueous composition comprising CsA in liposomally solubilized form at a concentration of about 4 mg/mL is administered, as described above.

The pharmaceutical compositions for use according to the invention can be administered according to a pre-determined dosing regimen. Especially, the composition can be administered a specific number of times during each week of treatment. For example, the pharmaceutical composition can be administered three times per week. Preferably, the formulation is administered daily. Even more preferred, the composition is administered twice daily.

In a further aspect, the present invention provides for a method for preventing or treating a pulmonary disease or condition in a subject, the method comprising the step of administering an inhalable immunosuppressive macrocyclic active ingredient to said subject by inhalation in form of an aerosol comprising the immunosuppressive macrocyclic active ingredient, wherein the aerosol is generated by nebulization of the pharmaceutical composition using a nebulizer (100), the nebulizer comprising:

a) an aerosol generator (101) comprising:
   a fluid reservoir (103) or an interface configured to connect a fluid reservoir, and
   a vibratable membrane (110) having a plurality of apertures, the apertures being adapted to produce an aerosol comprising droplets having a mass median aerodynamic diameter (MMAD) of up to about 4.0 µm as measured with a 0.9% (w/v) aqueous solution of sodium chloride;

b) a chamber (105) for temporarily accommodating the aerosol generated by the aerosol generator, the chamber having an inner lumen with a volume in the range of from about 50 to about 150 ml; and c) a mouthpiece (40) for delivering the aerosol supplied by the nebulizer 100 to the subject, the mouthpiece having an exhalation filter (30).

More specifically, the method for preventing or treating a pulmonary disease or condition may further comprise the step of providing a pharmaceutical composition comprising an inhalable immunosuppressive macrocyclic active ingredient in form of an aqueous liquid solution.

In connection with this further aspect of the present invention as well as with regard to the further aspects as described below, it is to be understood that all features, embodiments and aspects of the present invention as described in detail above for the first aspect of the invention as well as all combinations thereof equally apply in connection with the present method of treatment as well as for the uses of the pharmaceutical composition of the present invention as well as the kit as described further below.

In a third aspect, the present invention provides for the use of an inhalable immunosuppressive macrocyclic active ingredient in the manufacture of a pharmaceutical composition for the prevention or treatment of a pulmonary disease or condition in a subject by inhalation, wherein the pharmaceutical composition is administered to the subject by inhalation in form of an aerosol, wherein the pharmaceutical composition is administered to the subject by inhalation in form of an aerosol, and wherein the aerosol is generated by nebulization of the pharmaceutical composition using a nebulizer (100), the nebulizer comprising:

a) an aerosol generator (101) comprising:

a fluid reservoir (103) for holding the pharmaceutical composition or an interface configured to connect a fluid reservoir, and a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;

b) a chamber (105) for temporarily accommodating the aerosol generated by the aerosol generator (101), the chamber having an inner lumen with a volume in the range of from about 50 to about 150 ml; and c) a mouthpiece (40) for delivering the aerosol supplied by the nebulizer (100) to the subject, the mouthpiece having an exhalation filter (30).

In a fourth aspect, the present invention provides a kit comprising a pharmaceutical composition comprising an inhalable immunosuppressive macrocyclic active ingredient for use in the prevention or treatment of a pulmonary disease or condition in a subject; and a nebulizer (100), the nebulizer comprising:

a) an aerosol generator (101) comprising:

a fluid reservoir (103) for holding the pharmaceutical composition or an interface configured to connect a fluid reservoir, and a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;

b) a chamber (105) for temporarily accommodating the aerosol generated by the aerosol generator (101), the chamber having an inner lumen with a volume in the range of from about 50 to about 150 ml; and c) a mouthpiece (40) for delivering the aerosol supplied by the nebulizer (100) to the subject, the mouthpiece having an exhalation filter (30).

In specific embodiments of the kit according to this aspect of the invention, the pharmaceutical composition comprising an inhalable immunosuppressive macrocyclic active ingredient for use in the prevention or treatment of a pulmonary disease or condition in a subject is provided in form of a preformed liquid aqueous composition.

In further specific embodiments of the kit according to this aspect of the invention, the pharmaceutical composition comprising an inhalable immunosuppressive macrocyclic active ingredient for use in the prevention or treatment of a pulmonary disease or condition in a subject is provided in form of a lyophilisate comprising the inhalable immunosuppressive macrocyclic active ingredient and a sterile liquid aqueous carrier liquid for the reconstitution of the lyophilisate to form a liquid pharmaceutical composition.

The following list of numbered items are embodiments comprised by the present invention:

1. A pharmaceutical composition comprising an inhalable immunosuppressive macrocyclic active ingredient for use in the prevention or treatment of a pulmonary disease or condition in a subject, wherein the pharmaceutical composition is administered to the subject by inhalation in form of an aerosol, and wherein the aerosol is generated by nebulization of the pharmaceutical composition using a nebulizer (100), the nebulizer comprising:

a) an aerosol generator (101) comprising:

a fluid reservoir (103) for holding the pharmaceutical composition or an interface configured to connect a fluid reservoir, and a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;

b) a chamber (105) for temporarily accommodating the aerosol generated by the aerosol generator (101), the chamber having an inner lumen with a volume in the range of from about 50 to about 150 ml; and c) a mouthpiece (40) for delivering the aerosol supplied by the nebulizer (100) to the subject, the mouthpiece having an exhalation filter (30).

2. The pharmaceutical composition for use according to item 1, wherein the pulmonary disease or condition is selected from the group consisting of asthma, refractory asthma, chronic obstructive bronchitis, parenchymal, fibrotic and interstitial lung diseases and inflammations, bronchiolitis obliterans (BOS), and acute and chronic organ transplant rejection reactions after lung transplantation and the diseases resulting therefrom.

3. The pharmaceutical composition for use according to item 1 or 2, wherein the pulmonary disease or condition is bronchiolitis obliterans (BOS), optionally after acute and chronic organ transplant rejection reactions after lung transplantation or after hematopoietic stem cell transplantation (HSCT).

4. The pharmaceutical composition for use according to any of the preceding items, wherein the pulmonary disease or condition is bronchiolitis obliterans (BOS) grade I or higher, specifically BOS grade I or II, especially BOS grade I.

5. The pharmaceutical composition for use according to any of the preceding items, for use in the treatment of a pulmonary disease or condition in a subject.
6. The pharmaceutical composition for use according to any of the preceding items, wherein the inhalable immunosuppressive macrocyclic active ingredient is selected from cyclosporine A (CsA) and tacrolimus.
7. The pharmaceutical composition for use according to any of the preceding items, wherein the inhalable immunosuppressive active ingredient is cyclosporine A.
8. The pharmaceutical composition for use according to any of the preceding items, wherein the inhalable immunosuppressive active ingredient is present in liposomally solubilized form (L-CsA).
9. The pharmaceutical composition for use according to any of the preceding items, wherein the composition is a liquid composition comprising an aqueous liquid vehicle.
10. The composition for use according to item 9, wherein the aqueous liquid vehicle essentially consists of saline, preferably of saline with a concentration of 0.25% (w/v).
11. The pharmaceutical composition for use according to any preceding item, comprising the immunosuppressive macrocyclic active ingredient in a concentration in the range of from about 1 mg/mL to about 10 mg/mL.
12. The pharmaceutical composition for use according to any preceding item, wherein the liquid aqueous composition comprises cyclosporine A in liposomally solubilized form (L-CsA) in a concentration in the range of from about 3 mg/mL to about 5 mg/mL.
13. The pharmaceutical composition for use according to item 12, wherein the liquid aqueous composition comprises cyclosporine A in liposomally solubilized form (L-CsA) in a concentration in the range of from about 3.8 mg/mL to about 4.2 mg/mL.
14. The pharmaceutical composition for use according to any preceding item, wherein the aqueous liquid composition comprising the inhalable immunosuppressive macrocyclic active ingredient in liposomally solubilized form is obtained by reconstitution of a lyophilisate comprising the immunosuppressive macrocyclic active ingredient and liposome forming structures.
15. The pharmaceutical composition for use according to any preceding item, wherein the composition comprises at least one disaccharide selected from the group consisting of saccharose, lactose and trehalose, preferably saccharose.
16. The pharmaceutical composition for use according to item 15, wherein the composition has a content of the at least one disaccharide selected from the group consisting of saccharose, lactose and trehalose, preferably saccharose, in the range of from about 5 to about 15 wt.-%, preferably in the range of from about 7.5 to about 12.5 wt.-%, based on the total weight of the resulting pharmaceutical composition.
17. The pharmaceutical composition for use according to any of items 14 to 16, wherein the liposome-forming structures comprise a bilayer membrane formed of a membrane-forming substance selected from the group of phospholipids.
18. The pharmaceutical composition for use according to any of item 14 to 17, wherein the liposome-forming structures are at least partly present in unilamellar form.
19. The pharmaceutical composition for use according to any of items 14 to 18, wherein the inhalable immunosuppressive macrocyclic active ingredient is at least partially incorporated (or intercalated) in the bilayer membrane of the liposome-forming structures.
20. The pharmaceutical composition for use according to any of items 14 to 19, wherein the inhalable immunosuppressive macrocyclic active ingredient, specifically wherein CsA is predominantly (for example by at least about 90% or even at least about 95% to about 97.5%) incorporated in the bilayer membrane of the liposome-forming structures.
21. The pharmaceutical composition for use according to any of items 17 to 20, wherein the membrane-forming substance selected from the group of phospholipids is a mixture of natural phospholipids.
22. The pharmaceutical composition for use according to any of items 17 to 21, wherein the membrane-forming substance selected from the group of phospholipids is a lecithin containing unsaturated fatty acid residues.
23. The pharmaceutical composition for use according to any of items 17 to 22, wherein the membrane forming substance selected from the group of phospholipids is a lecithin selected from the group consisting of soy bean lecithin, Lipoid S75, Lipoid S100, Phospholipon® G90, 100 or a comparable lecithin.
24. The pharmaceutical composition for use according to any of items 14 to 23, wherein the composition further comprises at least one solubility-enhancing substance selected from the group of non-ionic surfactants.
25. The pharmaceutical composition for use according to item 24, wherein the at least one non-ionic surfactant is selected from the group of polysorbates.
26. The pharmaceutical composition for use according to item 24 or 25, wherein the solubility-enhancing substance selected from the group of non-ionic surfactants is polysorbate 80.
27. The pharmaceutical composition for use according to any of items 24 to 26, wherein the weight ratio of phospholipid to polysorbate is selected in the range of from about 15:1 to about 9:1, preferably between from about 14:1 to about 12:1, for example, about 13:1.
28. The pharmaceutical composition for use according to any of items 24 to 27, wherein the weight ratio between the (sum of the) phospholipid and the nonionic surfactant on the one hand and the inhalable immunosuppressive macrocyclic active ingredient, specifically cyclosporine A (CsA) on the other hand is selected in the range of from about 5:1 to about 20:1, preferably from about 8:1 to about 12:1 and more preferably about 10:1.
29. The pharmaceutical composition for use according to any of items 24 to 28, wherein the weight ratio between the phospholipid (lecithin), the nonionic surfactant and the inhalable immunosuppressive macrocyclic active ingredient, specifically cyclosporine A (CsA) is between about 15:1:1.5 and about 5:0.3:0.5, and preferably at about 9:0.7:1.
30. The pharmaceutical composition for use according to any preceding item, wherein the composition comprises one or more further excipients.
31. The pharmaceutical composition for use according to item 30, wherein the one or more further excipients are selected from buffers and chelating agents.

32. The pharmaceutical composition for use according to any preceding item, wherein the composition is in the form of a dispersion with an osmolality in the range of from about 430 to about 550 mOsmol/kg.
33. The pharmaceutical composition for use according to any preceding item, wherein the composition is in the form of a dispersion with a polydispersity index (PI) as measured by photon correlation spectroscopy up to about 0.50.
34. The pharmaceutical composition for use according to item 32 or 33, wherein the dispersion is essentially free from visible particles.
35. The pharmaceutical composition for use according to any of items 32 to 34, wherein the dispersion comprises liposomes with a z-average diameter as measured by photon correlation spectroscopy in the range of from about 40 to about 100 nm.
36. The pharmaceutical composition for use according to any preceding item, wherein the vibratable membrane (110) separates the fluid reservoir (103) and the chamber (105).
37. The pharmaceutical composition for use according to any preceding item, wherein the vibratable membrane (110) has a convex shape curving towards the aerosol release side of the membrane.
38. The pharmaceutical composition for use according to any preceding item, wherein the vibratable membrane (110) has from about 100 to about 400 apertures per $mm^2$.
39. The pharmaceutical composition for use according to any preceding item, wherein the plurality of apertures of the vibratable membrane (110) have a tapered shape narrowing towards the aerosol release side of the vibratable membrane.
40. The pharmaceutical composition for use according to any preceding item, wherein the apertures of the vibratable membrane (110) have an exit diameter of up to 4.0 μm as measured by scanning electron microscopy (SEM).
41. The pharmaceutical composition for use according to any preceding item, wherein the aerosol generator (101) comprises a piezoelectric element (such as a piezoelectric crystal as a vibration generator).
42. The pharmaceutical composition for use according to any preceding item, wherein the inhalable immunosuppressive macrocyclic active ingredient is delivered to the lungs (or the lung) of the subject in an amount (Delivered dose, DD) of at least 70%, more specifically in an amount in the range of from about 70% to about 80% of the amount administered to the subject.
43. The pharmaceutical composition for use according to any preceding item, wherein the inhalable immunosuppressive macrocyclic active ingredient is administered to the subject at a total output rate (TOR) of at least 200 mg/min, more specifically at a total output rate in the range of from about 200 to about 250 mg/min.
44. The pharmaceutical composition for use according to any preceding item, wherein the amount of the inhalable immunosuppressive macrocyclic active ingredient exhaled by the subject is up to 10%, more specifically from about 4% to about 8% of the total amount of active ingredient administered to the subject.
45. The pharmaceutical composition for use according to any preceding item, wherein the aerosol administered to the patient comprises droplets and wherein at least 50%, more specifically from about 60% to about 95% or more specifically from about 70% to about 90% of the total number of droplets have a diameter of up to 5 μm (as measured by laser diffraction or by a multistage cascade impactor as described above) when measured with a aqueous composition comprising L-CsA in a concentration of 4 mg/mL.
46. The pharmaceutical composition for use according to any preceding item, wherein 1 mL of the pharmaceutical composition comprising an inhalable immunosuppressive macrocyclic active ingredient is aerosolized (nebulized) within a period of up to about 5 min, specifically in cases in which a liquid aqueous composition comprising CsA in liposomally solubilized form at a concentration of 4 mg/mL is administered.
47. The pharmaceutical composition for use according to any preceding item, wherein the mouthpiece (40) comprises:
   a body (46) defining a fluid path (47) from an inlet port (41) connectable to the nebulizer (100) to an inhalation opening (42) to be received in the mouth of the user; and
   a filter (30) having a filter base (31) in fluid communication with the fluid path (47), a filter top (33) detachably connected to the filter base and a filter material (32) provided between the filter base and the filter top, wherein the filter top has an exhalation opening (36) cooperating with a one-way valve (39) allowing exhaustion of fluid from the fluid path through the filter material to the outside of the mouthpiece upon exhalation of a patient through the inhalation opening;
   wherein the body and the filter base are an integrated one-piece unit.
48. The pharmaceutical composition for use according to any of the preceding items, wherein the aerosol generator (101), the chamber (105) and the mouthpiece (40) are arranged in that order along the longitudinal direction of the nebulizer (100).
49. The pharmaceutical composition for use according to any of the preceding items, wherein the fluid reservoir (103) or the interface and the membrane (110) are arranged in that order along the longitudinal direction of the nebulizer (100).
50. The pharmaceutical composition for use according to any of the preceding items, wherein the chamber (105) has a length ($L_C$) along the longitudinal direction of the nebulizer between 20 mm and 100 mm, particularly 50 mm to 100 mm.
51. The pharmaceutical composition for use according to any of the preceding items, wherein the chamber (105) has an inner lumen with a volume in the range of from about 75 to about 125 ml.
52. The pharmaceutical composition for use according to any of the preceding items, wherein the chamber (105) cooperates with an ambient opening (113) having a one-way valve (114) allowing ambient air to enter the chamber (105) from outside of the nebulizer (100) upon inhalation of a subject through the inhalation opening (42) of the mouthpiece (40).
53. The pharmaceutical composition for use according to any of items 47 to 52, wherein the integrated one-piece unit of the body (46) and the filter base (31) are an integrated one-piece unit is an injection molded part.
54. The pharmaceutical composition for use according to any of items 47 to 53, wherein a distance (D) between the filter base (31) and the inhalation opening (42) of the mouthpiece (40) as seen in a side view is at least 30 mm, preferably at least 35 mm and not more than 50 mm, preferably not more 40 mm.

55. The pharmaceutical composition for use according to any of items 47 to 54, wherein a maximum height (H) of the mouthpiece (40) as seen in a side view is not more than 90 mm, preferably not more than 85 mm.

56. The pharmaceutical composition for use according to any of items 47 to 55, wherein a retaining rib (45) of the mouthpiece (40) for being engaged behind the teeth of a user is provided on an upper side of the body (46) and/or on a lower side of the body (46) adjacent to the inhalation opening (42).

57. The pharmaceutical composition for use according to any of items 47 to 56, wherein a front edge (51) of the body (46) surrounding the inhalation opening (42) is curved in a plan view and/or side view.

58. The pharmaceutical composition for use according to any of items 47 to 57, wherein the inlet port (41) is conical to be force-fittingly connectable to a boss (106) of the nebulizer (100).

59. The pharmaceutical composition for use according to any of items 47 to 58, wherein the inhalation opening (42) is oval-shaped in a front view, the oval shape having a minor axis and a major axis, wherein the filter base (31) extends from the body (46) in a direction along the minor axis.

60. A method for preventing or treating a pulmonary disease or condition in a subject, the method comprising the step of administering an inhalable immunosuppressive macrocyclic active ingredient to said subject by inhalation in form of an aerosol comprising the immunosuppressive macrocyclic active ingredient,
  wherein the aerosol is generated by nebulization of the pharmaceutical composition using a nebulizer (100), the nebulizer comprising:
  a) an aerosol generator (101) comprising:
    a fluid reservoir (103) or an interface configured to connect a fluid reservoir, and
    a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;
  b) a chamber (105) for temporarily accommodating the aerosol generated by the aerosol generator, the chamber having an inner lumen with a volume in the range of from about 50 to about 150 ml; and
  c) a mouthpiece (40) for delivering the aerosol supplied by the nebulizer 100 to the subject, the mouthpiece having an exhalation filter (30).

61. The method according to item 60, further comprising the step of
  providing a pharmaceutical composition comprising an inhalable immunosuppressive macrocyclic active ingredient in form of an aqueous liquid solution.

62. The use of an inhalable immunosuppressive macrocyclic active ingredient in the manufacture of a pharmaceutical composition for the prevention or treatment of a pulmonary disease or condition in a subject by inhalation, wherein the pharmaceutical composition is administered to the subject by inhalation in form of an aerosol,
  wherein the pharmaceutical composition is administered to the subject by inhalation in form of an aerosol, and
  wherein the aerosol is generated by nebulization of the pharmaceutical composition using a nebulizer (100), the nebulizer comprising:
  a) an aerosol generator (101) comprising:
    a fluid reservoir (103) for holding the pharmaceutical composition or an interface configured to connect a fluid reservoir, and
    a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;
  b) a chamber (105) for temporarily accommodating the aerosol generated by the aerosol generator (101), the chamber having an inner lumen with a volume in the range of from about 50 to about 150 ml; and
  c) a mouthpiece (40) for delivering the aerosol supplied by the nebulizer (100) to the subject, the mouthpiece having an exhalation filter (30).

63. A kit comprising
  a pharmaceutical composition comprising an inhalable immunosuppressive macrocyclic active ingredient for use in the prevention or treatment of a pulmonary disease or condition in a subject; and
  a nebulizer (100), the nebulizer comprising:
  a) an aerosol generator (101) comprising:
    a fluid reservoir (103) for holding the pharmaceutical composition or an interface configured to connect a fluid reservoir, and
    a vibratable membrane (110) having a plurality of apertures, the apertures being adapted to produce an aerosol comprising droplets having a mass median aerodynamic diameter (MMAD) of up to about 4.0 μm as measured with a 0.9% (w/v) aqueous solution of sodium chloride;
  b) a chamber (105) for temporarily accommodating the aerosol generated by the aerosol generator (101), the chamber having an inner lumen with a volume in the range of from about 50 to about 150 ml; and
  c) a mouthpiece (40) for delivering the aerosol supplied by the nebulizer (100) to the subject, the mouthpiece having an exhalation filter (30).

64. The kit according to item 63, wherein the pharmaceutical composition comprising an inhalable immunosuppressive macrocyclic active ingredient for use in the prevention or treatment of a pulmonary disease or condition in a subject is provided in form of a preformed liquid aqueous composition.

65. The kit according to item 64, wherein the pharmaceutical composition comprising an inhalable immunosuppressive macrocyclic active ingredient for use in the prevention or treatment of a pulmonary disease or condition in a subject is provided in form of a lyophilisate comprising the inhalable immunosuppressive macrocyclic active ingredient and a sterile liquid aqueous carrier liquid for the reconstitution of the lyophilisate to form a liquid pharmaceutical composition.

The following examples serve to illustrate the invention; however, these are not to be understood as restricting the scope of the invention:

EXAMPLES

Example 1

1.1 Step 1: Preparation of liposomal solution of cyclosporine A:

1.1.1 Approximately 70% (~104 L) water for injections was filled into the preparation vessel. It was degassed by introduction of nitrogen gas and warmed up to a temperature of 40 to 45° C. 18.0 kg of saccharose, 450.0 g of sodium dihydrogen phosphate dihydrate, 612.0 g of disodium hydrogen phosphate decahydrate and 36.0 g of disodium edetate were added together and approximately 5% (8.0 L) of water for injections were used for rinsing. The mixture was stirred until a visually clear solution was obtained. The solution was cooled down to 20 to 25° C. and 6480.0 g of soy bean lecithin S100 (Lipoid S100) was added and stirred until a homogenous dispersion was obtained. Then, 504.0 g of polysorbate 80 HP (Tween 80) was added under gentle stirring to avoid foaming and the container holding the polysorbate was rinsed with approximately 100 mL of water for injections. After that, 720.0 g of cyclosporine A and approximately 5% (8 L) of water for injections was added and the mixture was stirred until a homogenous dispersion was formed.

1.1.2 Following that, the resulting dispersion was cooled to a temperature of 5 to 10° C. and exposed to high pressure homogenization at a pressure of 100 bar (first stage) and 1000 bar (second stage), respectively, using a GEA high pressure homogenizer. The high-pressure homogenization was repeated 9 times (cycles).

1.1.3 The resulting homogenized suspension was then filtered through a bioburden reduction filter with a pore size of 0.2 μm in minimum once and transferred into a filling/storage tank.

1.2 Step 2: Aseptic Filling, Lyophilization and Packaging 1.2.1 Glass vials with a filling volume of 10 mL were sterilized in a hot-air sterilizing tunnel, cooled down and filled with aliquots of 1.35 mL (5 mg dosage) of the dispersion as prepared according to step 1 as described above after aseptic sterilisation using 2 sterile filters with a pore size of 0.2 μm between the filling/storage tank and the filling needles. The vials were then partially closed with sterilized lyophilization stoppers and loaded into a lyophilizer, i.e. a GEA Lyovac FCM and were lyophilized according to a 72 h lyophilization cycle.

1.2.2 After completion of lyophilization, the vials were automatically fully stoppered in the lyophilization chamber. The vials were unloaded and closed with flip-tear-off caps. Each vial contained approximately 190 mg of an almost white, homogenous, porous lyophilization cake containing 5 mg of cyclosporine A in liposomally solubilized form with a maximum residual moisture of 2% (w/w) and a shelf life of 3 years.

1.2.3 The composition of the lyophilized drug product prepared as described above is summarized in Table 1 below:

TABLE 1

| Ingredient | Quantity per unit | Quantity % (w/w) |
|---|---|---|
| Cyclosporine A | 5 mg | 2.69 |
| Polysorbate 80 | 3.5 mg | 1.88 |
| Lipoid S100 | 45 mg | 24.18 |
| Sucrose | 125 mg | 67.16 |
| Sodium dihydrogen phosphate dihydrate | 3.125 mg | 1.68 |
| Disodium hydrogen phosphate dodecahydrate | 4.25 mg | 2.28 |
| Disodium edetate dihydrate | 0.25 mg | 0.13 |
| Total | 186.125 mg | 100.00 |

Example 2: Reconstitution of the Lyophilized Composition Comprising Cyclosporine A to Yield a Colloidal Solution of Liposomally Solubilized Cyclosporine A for Nebulization and Inhalation 2.1 For the preparation of a colloidal solution with a content of liposomally solubilized cyclosporine A of 10 mg, an aliquot of 372.3 mg of the lyophilization cake as prepared according to Example 1 above was dissolved in 2.65 mL of a sterile aqueous sodium chloride solution with a concentration of 0.25% (w/v) to give an opalescent aqueous solution of liposomal cyclosporine A for inhalation purposes with a concentration of CsA of 4 mg/mL.

2.2 The composition of the reconstituted drug product prepared as described above is summarized in Table 2 below:

TABLE 2

| Ingredient | Quantity per unit | Quantity % (w/v) |
|---|---|---|
| Cyclosporine A | 10 mg | 0.4 |
| Polysorbate 80 | 7.5 mg | 0.28 |
| Lipoid S100 | 90 mg | 3.6 |
| Sucrose | 250 mg | 10 |
| Sodium dihydrogen phosphate dihydrate | 6.25 mg | 0.25 |
| Disodium hydrogen phosphate dodecahydrate | 8.5 mg | 0.34 |
| Disodium edetate dihydrate | 0.5 mg | 0.02 |
| Sodium chloride | 5.6 mg | 0.22 or 0.23 |
| Water for Injection | Ad 2.5 mL | Ad 100 |

Example 3

3.1 The breath simulation experiments were conducted according to Eur. Ph. 2.9.44 using a Compas 2 breath simulator (PARI GmbH, Germany) with a breathing pattern of 500 mL tidal volume at a frequency of 15 breaths/min and an inhalation/exhalation ratio of 50:50.

3.2 2.4 mL of the composition as described in Example 2.2 above were filled into an electronic vibrating membrane nebulizer having a membrane adapted to produce an aerosol with particle having a mass median aerodynamic diameter (MMAD) in the range of 2.4 to 4.0 μm when measured with a 0.9% (w/v) solution of aqueous sodium chloride. The nebulizer further had a mixing chamber with a volume of 94 mL. The nebulizer was connected to a sinus pump of the breath simulator. The drug containing aerosol droplets were collected on 2 consecutive inspiratory filter (polypropylene filter pad G300, PARI, in filter casing with a diameter of 6.5 cm). Between the inspiratory filter and the breath simulator a further filter was installed (BB50 TE, Pall Filtersystems GmbH, Germany).

3.3 After complete nebulization, the inhalation filters were removed, extracted and the extracts analyzed.

3.4 The results of breath simulation experiments as described above are summarized in Table 3 below:

TABLE 3

| | Mean value | Standard deviation (SD) |
|---|---|---|
| Total Output Rate (TOR) [mg/min] | 245 | 31 |
| Delivered Dose (DD) [mg] | 6.916 | 0.322 |
| Delivered Dose (DD) [%] | 72.0 | 3.4 |
| Exhaled amount [mg] | 0.899 | 0.271 |
| Exhaled amount [%] | 9.4 | 2.8 |
| Residue in nebulizer [mg] | 1.253 | 0.379 |
| Residue in nebulizer [%] | 13.1 | 4.0 |
| Respirable dose (RD ≤ 5 μm) [mg] | 5.620 | 0.465 |
| Respirable dose (RD ≤ 5 μm) [%] | 58.5 | 4.8 |
| End of aerosol production [min] | 9.64 | 1.62 |
| Automated shutoff [min] | 9.98 | 1.58 |

Example 4

4.1 In addition to this, the generated aerosol was characterized according to USP chapter <1601> resp. Ph. Eur. 2.9.44 using the Next Generation Impactor (Next Generation Cascade Impactor, NGI) to assess the aerodynamic droplet size distribution of the nebulized aerosols at an airflow of 15.0+/−0.7 L/min, an air temperature of 23.0 +/−2.0° C. and a relative humidity of 50.0+/−5.0%. The fill volume was 2.4 mL of the composition as described in Example 2.2. Deviating from the USP procedure the impactor temperature was adapted to the aerosol temperature (18.0+/−1.0° C.). The nebulizers with the mouthpieces attached were connected via a rubber connector to the induction port of the NGI. The nebulization was conducted and operated until the automatic shutoff of the nebulizer.

4.2 The results of the aerosol characterization experiments (n=5) as described above are summarized in Table 4 below:

TABLE 4

| | Mean value | Standard deviation (SD) |
|---|---|---|
| Mass median aerodynamic diameter (MMAD) [μm] | 3.26 | 0.24 |
| Geometric Standard Deviation (GSD) | 1.62 | 0.04 |
| Fine Particle Dose (FPD ≤ 5 μm) [mg] | 6.951 | 0.475 |
| Fine Particle Fraction (FPF ≤ 5 μm] [%] | 81.2 | 4.7 |
| End of aerosol production [min] | 10.1 | 1.18 |
| Automated shutoff [min] | 10.41 | 1.25 |

Comparative Example 1

Examples 3 and 4 were repeated using an eFlow® Rapid electronic nebulizer (PARI GmbH, Germany) having a vibratable membrane adapted to produce an aerosol with particle having a mass median aerodynamic diameter of 4.1 μm when measured with a 0.9% (w/v) solution of aqueous sodium chloride. The nebulizer further had a mixing chamber with a volume of 48 mL. The results are summarized in Table 5 below:

TABLE 5

| | Mean value | Standard deviation (SD) |
|---|---|---|
| Total Output Rate (TOR) [mg/min] | 192 | 17 |
| Mass median aerodynamic diameter (MMAD) [μm] | 3.25 | 0.15 |
| Geometric Standard Deviation (GSD) | 1.54 | 0.02 |
| Fine Particle Fraction (FPF ≤ 5 μm) [%] | 86.7 | 2.2 |
| Delivered Dose (DD) [mg] | 3.649 | 0.253 |
| Delivered Dose (DD) [%] | 36.5 | 2.5 |
| Exhaled amount [mg] | 1.287 | 0.486 |
| Exhaled amount [%] | 12.9 | 4.9 |
| Residue in nebulizer [mg] | 4.704 | 0.407 |
| Residue in nebulizer [%] | 47.0 | 4.1 |
| Respirable dose (RD ≤ 5 μm) [mg] | 3.161 | 0.182 |
| Respirable dose (RD ≤ 5 μm) [%] | 31.6 | 1.8 |
| End of aerosol production [min] | 6.80 | 0.54 |
| Automated shutoff [min] | 7.01 | 0.60 |

The invention claimed is:

1. A method of delaying the onset or treatment of a pulmonary disease or condition in a subject, the method comprising administering a pharmaceutical composition comprising a therapeutically effective amount of cyclosporine A in liposomally solubilized form to the subject, wherein the composition is a liquid composition comprising an aqueous liquid vehicle, wherein the pharmaceutical composition is administered to the subject by a nebulizer, the nebulizer comprising:

a) an aerosol generator adapted to produce an aerosol comprising droplets having a mass median aerodynamic diameter of up to about 4.0 um as measured with a 0.9% (w/v) aqueous solution of sodium chloride;

b) a chamber having a volume in the range of from about 50 to about 150 ml; and c) a mouthpiece;

wherein the mouthpiece comprises:

a body; and an exhalation filter comprising a filter base;

wherein the body and the filter base are an integrated one-piece unit.

2. The method according to claim 1, wherein the pulmonary disease or condition is selected from the group consisting of asthma, refractory asthma, chronic obstructive bronchitis, parenchymal, fibrotic and interstitial lung diseases and inflammations, bronchiolitis obliterans, and acute and chronic organ transplant rejection reactions after lung transplantations and the diseases resulting therefrom.

3. The method according to claim 1, wherein the pulmonary disease or condition is bronchiolitis obliterans grade I or higher.

4. The method according to claim 1, wherein the composition comprises cyclosporine A in a concentration in the range of from about 1 mg/mL to about 10 mg/mL.

5. The method according to claim 1, wherein the composition comprises cyclosporine A in liposomally solubilized form in a concentration in the range of from about 3 mg/mL to about 5 mg/mL.

6. The method according to claim 1, wherein the aqueous liquid composition comprising cyclosporine A in liposomally solubilized form is obtained by reconstitution of a lyophilisate comprising cyclosporine A and liposome forming structures.

7. The method according to claim 6, wherein the liposome-forming structures comprise a bilayer membrane formed of a membrane-forming substance selected from the group of phospholipids.

8. The method according to claim 7, wherein the membrane-forming substance selected from the group of phospholipids is a mixture of natural phospholipids.

9. The method according to claim 7, wherein the membrane-forming substance selected from the group of phospholipids is a lecithin containing unsaturated fatty acid residues.

10. The method according to claim 7, wherein the membrane forming substance selected from the group of phospholipids is selected from the group consisting of a soybean lecithin, a soybean phospholipid with 70% phosphatidylcholine content, and a soybean phospholipid with ≥94.0% phosphatidylcholine content.

11. The method according to claim 10, wherein the composition further comprises at least one solubility-enhancing substance selected from the group of non-ionic surfactants.

12. The method according to claim 11, wherein the at least one non-ionic surfactant is selected from the group of polysorbates.

13. The method according to claim 11, wherein the solubility-enhancing substance selected from the group of non-ionic surfactants is polysorbate 80.

14. The method according to claim 12, wherein the weight ratio of phospholipid to polysorbate is selected in the range of from about 15:1 to about 9:1.

15. The method according to claim 1, wherein the composition comprises at least one disaccharide selected from the group consisting of saccharose, lactose and trehalose.

16. The method according to claim 9, wherein the cyclosporine A is at least partially incorporated or intercalated in the bilayer membrane of the liposome-forming structures.

17. The method according to claim 1, wherein the aerosol generator comprises a vibratable membrane having a plurality of apertures, and wherein the vibratable membrane has from about 100 to about 400 apertures per $mm^2$.

18. The method according to claim 17, wherein the plurality of apertures of the vibratable membrane have a tapered shape narrowing towards the aerosol release side of the vibratable membrane.

19. The method according to claim 17, wherein the apertures of the vibratable membrane have an exit diameter in the range of from about 1.5 um to about 3.0 um as measured by scanning electron microscopy.

20. The method according to claim 1, wherein the aerosol administered to the subject comprises droplets and wherein from about 60% to about 95% of the total number of droplets have a diameter of up to 5 um when measured with an aqueous composition comprising cyclosporine A in liposomally solubilized form in a concentration of 4 mg/mL.

21. The method according to claim 1, wherein cyclosporine A in liposomally solubilized form is administered to the subject at a total output rate of at least 200 mg/min.

22. The method according to claim 1, wherein the amount of the cyclosporine A in liposomally solubilized form exhaled by the subject is up to 10%.

23. The method according to claim 1, wherein 1 mL of the pharmaceutical composition comprising the cyclosporine A in liposomally solubilized form is aerosolized within a period of up to about 5 min.

24. The method according to claim 15, wherein the at least one disaccharide is saccharose.

25. The method according to claim 22, wherein the amount of the cyclosporine A in liposomally solubilized form exhaled by the subject is from about 4% to about 8% of the total amount of active ingredient administered to the subject.

26. A method of delaying the onset or treatment of a pulmonary disease or condition in a subject, the method comprising administering a pharmaceutical composition comprising cyclosporine A in liposomally solubilized form to the subject, wherein the pharmaceutical composition is administered to the subject by a nebulizer, the nebulizer comprising:

a) an aerosol generator;

b) a chamber; and c) a mouthpiece;

wherein the mouthpiece comprises:

a body; and an exhalation filter comprising a filter base;

wherein the body and the filter base are an integrated one-piece unit; and wherein the aerosol generator, chamber and mouthpiece are adapted to deliver the cyclosporine A in liposomally solubilized form to a lung or lungs of the subject in an amount of at least 70%.

27. The method according to claim 26, wherein the cyclosporine A in liposomally solubilized form is delivered to one or more lungs of the subject in an amount in the range of from about 70% to about 80% of the amount administered to the subject.

* * * * *

UNITED STATES PATENT AND TRADEMARK OFFICE

CERTIFICATE OF CORRECTION

PATENT NO. : 12,263,247 B2
APPLICATION NO. : 18/391712
DATED : April 1, 2025
INVENTOR(S) : Oliver Denk It is certified that error appears in the above-identified patent and that said Letters Patent is hereby corrected as shown below:

In the Claims

Column 40, Line 35; Column 41, Line 48; and Column 42, Line 4, delete “um”, each occurrence, and insert --μm--.

Column 41, Line 34, for the claim reference numeral delete “9”, and insert --6--.

Signed and Sealed this
First Day of July, 2025

Coke Morgan Stewart
*Acting Director of the United States Patent and Trademark Office*